United States Patent [19]

Artavanis-Tsakonas et al.

[11] Patent Number: 5,780,300
[45] Date of Patent: Jul. 14, 1998

[54] MANIPULATION OF NON-TERMINALLY DIFFERENTIATED CELLS USING THE NOTCH PATHWAY

[75] Inventors: Spyridon Artavanis-Tsakonas, Hamden; Mark Edward Fortini; Kenji Matsuno, both of New Haven, all of Conn.

[73] Assignee: Yale University, New Haven, Conn.

[21] Appl. No.: 537,210

[22] Filed: Sep. 29, 1995

[51] Int. Cl.$^6$ .............................. C12N 5/08; C12N 5/02; C12N 5/06
[52] U.S. Cl. .................... 435/377; 435/325; 435/366; 435/372; 435/375
[58] Field of Search ........................ 435/6, 69.1, 325, 435/366, 372, 377, 375

[56] References Cited

U.S. PATENT DOCUMENTS 5,226,914 7/1993 Caplan et al. ........................ 623/16
5,580,738 12/1996 Laborda ................................ 435/6

FOREIGN PATENT DOCUMENTS

92/19734 11/1992 WIPO.
92/22584 12/1992 WIPO.
93/12141 6/1993 WIPO.
94/07474 4/1994 WIPO.
94/07522 4/1994 WIPO.
94/08037 4/1994 WIPO.
94/13701 6/1994 WIPO.
95/19779 7/1995 WIPO.

OTHER PUBLICATIONS

Ahmad et al., 1995, "Involvement of Notch–1 in mammalian retinal neurogenesis: Association of Notch–1 activity with both immature and terminally differentiated cells", Mech. Dev. 53:73–85.

Artavanis–Tsakonas et al., 1995, "Notch signaling", Science 268:225–232.

Austin et al., 1995, "Vertebrate retinal ganglion cells are selected from competent progenitors by the action of Notch–"Development 121:3637–3650.

Axelrod et al., 1996, "Interaction between Wingless and Notch signaling pathways mediated by Dishevelled", Science 271:1826–1832.

Bettenhausen et al., 1995, "Transient and restricted expression during mouse embryogenesis of Dll1, a murine gene closely related to Drosophila Delta", Development 121:2407–2418.

Bierkamp et al., 1993, "A zebrafish homologue of the Drosophila neurogene and its pattern of transcription during early embryo genesis", Mech Dev. 43:87–100.

Brou et al., 1994, "Inhibition of the DNA–binding activity of Drosophila Suppressor of Hairless and of its human homolog, KBF–2/RBP–Jk, by direct protein–protein interaction with Drosophila Hairless", Genes Dev. 8:2491–2503.

Cagan and Ready, 1089, "Notch is required for successive cell decisions in the developing Drosophila retina", Genes Dev. 3:1099–1112.

Chenn and McConnell, 1995, "Cleavage orientation and the asymmetric inheritance of Notch 1 immunoreactivity in mammalian neurogenesis", Cell. vol. 82:631–641.

Chitnis et al., 1993, "Primary neurogenesis in Xenopus embryos regulated by a homologue of the Drosophila neurogenic gene Delta ", Nature 375:761–766.

Coffman et al., 1993, "Expression of an exracellular deletion of Xotch diverts cell fate in Xenopus embryos", Cell 73:659–679.

Corbin et al., 1991, "A role for the Drosophila neurogenic genes in mesoderm differentiation", Cell 67:311–323.

Cummings and Cronmiller, 1994, "The daughterless gene functions together with Notch and Delta in the control of ovarian follicle development in Drosophila ", Development 120:381–394.

Delidakis et al., 1991, "Two genetically and molecularly distinct functions involved in early neurogenesis reside within the enhancer of split locus of Drosophila melanogaster ", Genetics 129:803–823.

Dorsky et al., 1995, "Xotch inhibits cell differentiation in the Xenopus retina", Neuron 14:487–496.

Ellison et al., 1991, "Tan–1 , the human homolog of the Drosophila Notch gene, is broken by chromosomal translocations in T lymphoblastic neoplasms", Cell 66:649–661.

Fehon et al., "Molecular interactions between the protein products of the neurogenic loci Notch and Delta , two EGF–homologous genes in Drosophila ", Cell 61:523–534.

Fehon et al., 1991, "Complex cellular and subcellular regulation of Notch expression during embryonic and imaginal development of Drosophila : Implications for Notch function", J. Cell. Biol. 113:657–669.

Fleming et al., 1990, "The gene Serrate encodes a putative EGF–like transmembrane protein essential for proper ectodermal development in Drosophila melanogaster", Genes and Development 1:2188–2201.

Fortini et al., 1993, "An activated Notch receptor blocks cell–fate commitment in the developing Drosophila eye", Nature 365:555–557.

Fortini et al., 1993, "Notch: neurogenesis is only part of the picture", Cell 75:1245–1247.

(List continued on next page.)

Primary Examiner—Nancy Degen
Attorney, Agent, or Firm—Pennie & Edmonds LLP

[57] ABSTRACT

The present invention is directed to methods for the expansion of non-terminally differentiated cells ("precursor cells") using agonists of Notch function, by inhibiting the differentiation of the cells without inhibiting proliferation (mitotic activity) such that an expanded population of non-terminally differentiated cells is obtained. The cells are preferably stem or progenitor cells. These expanded cells can be used in cell replacement therapy to provide desired cell populations and help in the regeneration of diseased and/or injured tissues. The expanded cell populations can also be made recombinant and used for gene therapy, or can be used to supply functions associated with a particular precursor cell or its progeny cell.

40 Claims, 12 Drawing Sheets

OTHER PUBLICATIONS

Fortini et al., 1994, "The suppressor of hairless protein participates in Notch receptor signaling", Cell 79:273–282.

Fortini et al., 1992, "Signalling by the *sevenless* protein tyrosine kinase is mimicked by *Ras 1* activation", Nature 355:559–561.

Franco del Amo et al., 1992, "Expression pattern of Motch, a mouse homolog of *Drosophila Notch* , suggests an important role in early postimplantation mouse development", Development 115:737–744.

Giniger et al., 1993, "Specifying the path of the intersegmental nerve of the *Drosophila* embryo: a role for *Delta and Notch*", Development 117:431–440.

Goldspiel et al., 1993, "Human gene therapy"Clin. Pharm. 12:488–505.

Goshima et al., 1991, "the osteogenic potential of culture-expanded rat marrow mesenchymal cells assayed in vivo in calcium phosphate ceramic bolcks", Clin. Orthop. 262:298–311.

Greenwald and Rubin, 1992, "Making a difference: the role of cell–cell interactions in establishing separate identities for equivalent cells", Cell 68:271–281.

Greenwald, 1994, "Structure/function studies of *lin –12/Notch proteins* ", Curr. Opin. Genet. Dev. 4: 556–562.

Hartenstein et al., 1992, "The function of the neurogenic genes during epithelial development in the *Drosophila* embryo", Development, 116:1203–1220.

Hartenstein and Prosakony, 1990, "A dual function of the *Notch* gene in *Drosophila* sensillum development", Dev. Biol. 142:13–30.

Henrique et al., 1995, "Expression of a Delta homologue in prospective neurons in the chick", Nature 375:787–790.

Hing et al., 1994, "Modulation of wingless signaling by *Notch* in *Drosophila* ", Mech. Dev. 47:261–268.

Horvitz et al., 1991, "Multiple intercellular signalling systems control the development of the *Caenorhabditis elegans* vulva", Nature 351:535–541.

Jan et al., 1993, "Functional gene cassettes in developmant", Proc. Natl. Acad. Sci. USA 90:8305–8307.

Johansen et al., 1989, "The *Notch* gene product is a glycoprotein expressed on the cell surface of both epidermal and neuronal precursor cells during *Drosophila* development", J. Cell. Biol. 109:2427–2440.

Kidd et al., 1989, "Structure and distribution of the *Notch* protein in the development *Drosophila* ", Genes Dev. 3:1113–1129.

Kidd et al., 1986, "Sequence of the *Notch* locus of *Drosophila melanogaster* : Relationship of the encoded protein to mammalian clotting and growth factors", Mol. Cell. Biol. 6:3094–3108.

Knust et al., 1992, "Seven genes of the *Enhancer of split* complex of *Drosophila melanogaster* encode helix–loop–helix proteins"Genetics 132:505–518.

Kopan et al., 1993, "Mouse *Notch* : expression in hair follicles correlates with cell fate determination", J. Cell. Biol. 121:631–641.

Kopan et al., 1994, "The intracellular domain of mouse *Notch* : a constitutively activated repressor of myogenesis directed at the basic helix–loop–helix region of MyoD", Development 120:2385–2396.

Kopczynski et al., "Delta, a *Drosophila* neurogenic gene, is transcriptionally complex and encodes a protein related to blood coagulation factors and epidermal growth factor of vertebrates", Genes and Development 2:1723–1735.

Lardelli et al., 1993, "MotchA and MotchB —two mouse *Notch* homologues are expressed in a wide variety of tissues", Exp. Cell Res. 204:364–372.

Lardelli et al., 1994, "The novel *Notch* homologue mouse *Notch3* lacks specific epidermal growth factor–repeats and is expressed in proliferating neuroepithelium", Mech Dev. 46:123–136.

Larsson et al., 1994, "The human *Notch 1,2, and 3* genes are located at chromosome positions 9q34, 1p13–p11, and 19p13.2–p13.1 in regions of neoplasia–associated translocation", Genomics 24:253–258.

Le Douarin et al., 1975, "Cholinergic differentiation of presumptive adrenergic neuroblasts in interspecific chimeras after heterotropic transplantations", Proc. Natl. Acad. USA 72:728–732.

Leff, 1995, "NIH proposes to grant ImClone license to tumor–targeting epidermal GF gene", BioWorld Today 6:2.

Lieber et al., 1993, "Antineurogenic phenotypes induced by truncated *Notch* proteins indictate a role in signal transduction and may point to a novel function for *Notch* in nuuclei", Genes and Development 7:1949–1965.

Lindsell et al., 1995, "Jagged: A mamalian ligand that activates *Notch1* "Cell 80:909–917.

Lindvall et al., 1990, "Grafts of fetal dopamine neurons survive and improve motor function in Parkinson's disease", Science 247:574–577.

Liu et al., 1996, "Epithelial expression and chromosomal location of human TLE genes: implications for Notch signaling and neoplasia", Genomics 31:58–64.

Lyman et al., 1993, "Further evidence for function of the *Drosophila Notch* protein as a transmembrane receptor", Proc. Natl. Acad. Sci. USA 90:10395–10399.

Markopoulo and Artavanis–Tsakonas, 1989, "The expression of the neorogenic locus *Notch* during the postembryonic development of *Drosophila melanogaster* and its relationship to mitotic activity", J. Neurogenetics 6:11–26.

Matsuno et al., 1995, "Deltex acts as a positive regulator of *Notch* signaling through interactions with the *Notch* ankyrin repeats", Development 121:2633–2644.

Morgan et al., 1993, "Human gene therapy", Annu. Rev. Biochem. 62:191–217.

Mulligan, 1993, "The basic science of gene therapy", Science 260:926–932.

Nusse and Varmus, 1992, "*Wnt* genes", Cell 69:1073–1087.

Rakic et al., 1982, "Early development events: cell lineages, acquisition of neuronal positions, and areal and laminar development", Neuroscience Res. Prog. Bull. 20:439–451.

Reaume et al., 1992 "Expression analysis of a *Notch* homologue in the mouse embryo", Dev. Biol. 154:377–387.

Roehl and Kimble, 1993, "Control of cell fate in C. *elegans* by a GLP–1 peptide consisting primarily of ankyrin repeats", Nature 364:632–635.

Ruohola et al., 1991, "Role of neurogenic genes in establishment of follicle and cell fate and oocyte polarity during oogenesis in *Drosophila*", Cell 66:433–449.

Schweisguth and Posakony, 1994, "Antagonistic activities of *Suppressor of Hairless and Hairless* control alternative cell fates in the *Drosophila* adult epidermis"Development 120:1433–1441.

Smoller et al., 1990, "The *Drosophila* neurogenic locus *mastermind*encodes a nuclear protein unusually rich in amino acid homopolymers", Genes Dev. 4:1688–1700.

Sternberg et al., 1993, "Falling off the knife edge", Curr. Bio. 3:763–765.

Stifani et al., 1992, "Human homologs of a *Drosophila Enhancer of split* gene product define a novel family of nuclear proteins", Nature Genet. 2:119–127.

Struhl et al., 1993, "Intrinsic activity of the Lin-12 and *Notch* intracellular domains in vivo", Cell 74:331.

Struhl and Basler, 1993, "Organizing activity of wingless protein in *Drosophila*", Cell 72:527–540.

Sun and Artavanis–Tsakonas, 1996, "The intracellular deletions of Delta and Serrate define dominant negative forms of the *Drosophila* Notch ligands", Development 122:2465–2474.

Swiatek et al., 1994, "*Notch1* is essential for the postimplantation development in mice", Genes Dev. 8:707–719.

Weinmaster et al., 1992, "*Notch2* : a second mammalian *Notch* gene", Development 116:931–941.

Weinmaster et al., 1991, "A homolog of *Drosophila Notch* expressed during mammalian development", Development 113:199–205.

Wharton et al., 1985, "Nucleotide sequence from the neurogenic locus *Notch* implies a gene product that shares homology with proteins containing EGF–like repeats", Cell 43:567–581.

Wu et al., 1991, "Delivery sysems for gene therapy", Biotherapy 3:87–95.

Xu et al., 1992, "The involvement of the *Notch* locus in *Drosophila* oogenesis", Development 115:913–922.

Zagouras et al., 1995, "Alterations in *Notch* signaling in neoplastic lesions of the human cervix", Proc. Natl. Acad. Sci. USA 92:6414–6418.

Orkin et al. Report & Recommendations of The Panel to Asses the NIH Investment in Research on Gene Therapy 1995.

```
SNPCQHGATC  SDFIGGYRCE  CVPGYQGVNC  EYEVDECQNQ  PCQNGGTCID  LVNHFKCSSCP  PGTRGLLCEE  NIDDC  AR---
PSPCQNGATC  TDYLGGYSCK  CVAGYHGVNC  SEEIDECLSH  PCQNGGTCLD  LPNTYKCSSCP  RGTQGVHCEI  NVDDC  NPPVD
PNPCQNGATC  TDYLGGYSCE  CVAGYHGVNC  SEEINECLSH  PCQNGGTCID  LINTYKCSSCP  RGTQGVHCEI  NVDDC  TPFYD
SQPCQNGGTC  RDLIGAYECQ  CRQGFQGQNC  ELNIDDCAPN  PCQNGGTCHD  RVMNFSCSCP   PGTMGLICEI  NKDDC  KP---
                                                                                                      1297
                                                                                                      1301
                                                                                                      1299
                                                                                                      1330

----GPHCLN  GGQCMDRIGG  YSCRCLPGFA  GERCEGDINE  CLSNPCSSEG  SLDCIQLTND  YLCVCRSAFT
PVSRSPKCFN  NGTCVDQVGG  YSCTCPPGFV  GERCEGDVNE  CLSNPCDARG  TQNCVQRVND  FHCECRAGHT
SFTLEPKCFN  NGKCIDRVGG  YNCICPPGFV  GERCEGDVNE  CLSNPCDSRG  TQNCIQLVND  YRCECRQGFT
----GACHN   NGSCIDRVGG  FECVCQPGFV  GARCEGDINE  CLSNPCSNAG  TLDCVQLVNN  YHCNCRPGHM

GRHCETFVDV  CPQMPCLNGG  TCAVASNMPD  GFTCRCPPGF  SGARCQS---  SCGQVKCRKG  EQCVHTAS--  GPRCFCPSP-
GRRCESVING  CKGKPCKNGG  TCAVASNTAR  GFICKCPAGF  EGATCENDAR  TCGSLRCLNG  GTCISGPR--  SPTCLLCLGPF
GRRCESVVDG  CKGMPCRNGG  TCAVASNTER  GFICKCPPGF  DGATCEYDSR  TCSNLRCQNG  GTCISVLT--  SSKCVCSEGY
GRHCEHKVDF  CAQSPCNGG   NCNI---RQS  GHHCICNNGF  YGKNCELSGQ  DCDSNPCRVG  -NCVVADEGF  GYRCECPRGT

--RDCES---  -GC-ASSPCQ  HGGSCHPQRQ  PPYYSCQCAP  PFSGSRCEI-  -YTAPP----  -S-----TPP   1422
TGPECQFPAS  SPCLGGNPCY  NQGTCEPTSE  SPFYRCLCPA  KFNGLLCHIL  DYSFGG----  -GAGRDIPPP   1444
TGATCQYPVI  SPC-ASHPCY  NGGTCQFFAE  EPFFQCFCPK  NFNGLFCHIL  DYEFPG----  -GLGKNITPP   1441
LGEHCEIDTL  DEC-SPNPCA  QGAACEDLLG  D--YECLCPS  KWKGKRCDIY  DANYPGWNGG  SGSGNDRYAA   1473

Lin-12/Notch Repeats
---A---TCL  SQYCADKARD  GVCDEACNSH  ACQWDGGDCS  LTMENPWANC  SSPLPCWDYI  NN-QCDELCN  TVECLFDNFE
LIEE---ACE  LPECQEDAGN  KVCSLQCNNH  ACGVDGGDCS  LNFNDPWKNC  TQSLQCWKYF  SDGHCDSQCN  SAGCLFDGFD
DNDD----ICE NEQCSELADN  KVCNANCNNH  ACGWDGGDCS  LNFNDPWKNC  TQSLQCWKYF  NDGKCDSQCN  NTGCLYDGFD
DLEQQRAMCD  KRGCTEKQGN  GICDSDCNTY  ACNFDGNDCS  LGI-NPWANC  TAN-ECWNKF  KNGKCNEECN  NAACHYDGHD
```

FIG.4A

```
CQGNSKTCK- -YDKYCADHF KDNHCNQGCN SEECGWDGLD CAADQPEN-L AEGTLVIVVL MPPEQLLQDA      1562
CQRAEGQCNP LYDQYCKDHF SDGHCDQGCN SAECEVDGLD CAEHVPER-L AAGTL-VVVV LMPPEQLRNS      1589
CQKVEVQCNP LYDQYCKDHF QDGHCDQGCN NAECEVDGLD C-ANMPEN-L AEGTLVLVVL MPPERLKNNS      1586
CERKLKSCDS LFDAYCQKHY GDGFCDYGCN NAECSVDGLD CENKTQSPVL AEGAMSVVML MNVEAFREIQ      1621

R-SFLRALGT LLHTNLRIKR DSQGELMVYP YYGEKSAAMK KQ--R---- ---------- ---MTRRSL PGEQ----E
SFHFLRELSR VLHTNVVFKR DAHGQQMIFP YYGREEELRK HPIKRAAEGW AAPDALLGQV KASLLPGGSE GGRRRRELDP
V-NFLRELSR VLHTNVVFKK DSKGEYKIYP YYGNEEELKK HHIKRSTDYW SDAPSAI--- -FSTMKESIL LGRHRRELDE
A-QFLRNMSH MLRTTVRLKK DALGHDIIIN WKDNVRVPEI EDTDFARKNK ILYTQQVHQ- ---------- ---------

TM
QEVAGSKVFL EIDNRQCVQD SDHCFKNTDA AAALLASHAI QG---TLSYP LVSVVSESLT PERT-Q-LLY       1680
MDVRGSIVYL EIDNRQCVQA SSQCFQSATD VAAFLGALAS LGSL-NIPYK IEAVQSETVE PPPPAQ-LHF       1737
MEVRGSIVYL EIDNRQCYKS SSQCFNSATD VAAFLGALAS LGSLDTLSYK PW-EDSVGLK TPKPST-LYP       1730
---TGIQIYL EIDNRKCTEC FTHAVEAAEF LAATAAKHQL RNDFQ-IHSV RGIKNPGDED NGEPPANVKY       1745

LLAVAVVIIL FIILLGVIMA KRKRK--HGS LWLPEGFTLR RDASNHKRRE PVGQDAVGLK NLSVQVSEAN LIGTGTSEHW
MYVAAAAFVL LFFVGCGVLL SRKRRRQHGQ LWFPEGFKV- SEASKKKRRE ELGEDSVGLK PLK-NASDGA LMDDNQNE-W
MLSMLVIPLL IIFVFMMVIV NKKRRREHDS FGSPTALFQK NPA-KRNGET PW-EDSVGLK PIK-NMTDGS FMDDNQNE-W
VITGIILVII ALAFFGMVL- STQRKRAHGV TWFPEGFRAP AAVMSRRRRD PHGQEMRNLN KQVAMQSQGV GQPGAH---W

VDDE------ ---------G PQPKKVKAED EALLSE-EDD PIDRRPWTQQ HLEAADIRRT PSLALTPPQA      1812
GDED------ ---------- LETKKFRFEE PVVLPD-LDD QTDHRQWTQQ HLDAADL-RM SAMAPTPPQG      1866
GDEET----- ---------- LENKRFRFEE QVILPELVDD KTDPRQWTRQ HLDAADL-RI SSMAPTPPQG      1860
SDDESDMPLP KRQRSDPVSG VGLGNNGGYA SDHTMVSEYE EADQRVWSQA HLDVVDV-R- AIM--TPP-A      1886
```

FIG.4B

```
CDC10/Ankyrin Repeats
EQEVDVLDVN VRGPDGCTPL MLASLRGGSS DLSDEDEDAE DSSANIITDL VYQGASLQAQ TFRTGEMALH LAARYSRADA
EVDADCMDVN VRGPDGFTPL MIASCSGGGL ETGNSEEE-E DAPA-VISDF IYQGASLHNQ TDRTGETALH LAARYSRSDA
EIEADCMDVN VRGPDGFTPL MIASCSGGGL ETGNSEEE-E DASANMISDF IGQGAQLHNQ TDRTGETALH LAARYARADA
HQDGGKHDVD ARGPCGLIPL MIAAVRGGGL DIGEDIENNE DSTAQVISDL LAQGAELNAT MDKTGETSLH LAARFARADA AKRLLDAGAD ANAQDNMGRC PLHAAVAADA QGVFQILIRN RVTDLDARMN DGTTPLILAA RLAVEGMVAE  1962
AKRLLEASAD ANIQDNMGRT PLHAAVSADA QGVFQILIRN RATDLDARMH DGTTPLILAA RLAVEGMLED  2014
AKRLLESSAD ANVQDNMGRT PLHAAVAADA QGVFQILIRN RATDLDARMF DGTTPLILAA RLAVEGMVEE  2009
AKRLLDAGAD ANCQDNTGRT PLHAAVAADA MGVFQILLRN RATNLNARMH DGTTPLILAA RLAIEGMVED  2036

LINCQADVNA VDDHGKSALH WAAAVNNVEA TLLLLKNGAN RDMQDNKEET PLFLAAREGS YEAAKILLDH FANRDITDHM  2097
LINSHADVNA VDDLGKSALH VAAAVNNVDA AVVLLKNGAN KDMQNNREET PLFLAAREGS YETAKVLLDH FANRDITDHM  2153
LINAHADVNA VDEFGKSALH VAAAVNNVDA AAVLLKNSAN KDMQNNKEET SLFLAAREGS YETAKVLLDH YANRDITDHM  2147
LITADADINA ADNSGKTALH WAAAVNNTEA VNILLMHHAN RDAQDDKDET PLFLAAREGS YEACKALLDN FANREITDHM  2185

DRLPRDVARD RMHHDIVRLL DEYNVTPSPP --GTVL--TS ALSPV----- -----ICGP NRSFLSLKHT  2097
DRLPRDIAQE RMHHDIVRLL DEYNLVRSPQ LHGAPLGGTP TLSPP----- -----LCSP NGYLGSLKPG  2153
DRLPRDIAQE RMHHDIVHLL DEYNLVKSPT LHNGPLGAT- TLSPP----- -----ICSP NGYMGNMKPS  2147
DRLPRDVASE RLHHDIVRLL DE-HVPRSPQ MLSMTPQAMI GSPPPGQQQP QLITQPTVIS AGNGGNNGNG  2185
```

FIG.4C

```
                                                         NLS                              CKII   cdc2   cdc2
PMGKKSRRPS AKSTMPTSLP NLAKEAKDAK GSRRKKSLSE KVQLSE--SS VTLSPVDSLE SPHTYVSDTT SSPM----
VQGKKVRKPS SKGLACGS-- ---KEAKDLK A-RRKKSQDG KGCLLD--SS GMLSPVDSLE SPHGYLSDVA SPPL----
VQSKKARKPS IKGNGC---- ---KEAKELK A-RRKKSQDG KTTLLDSGSS GVLSPVDSLE STHGYLSDVS SPPL----
NASGKQSNQT AKQKAA---- ---KKAKLIE GS-PDNGLDA TGSLRRKASS KKTSAASKKA ANLNGLNPGQ LTGGVSGVPG
                                            BNTS
                                                                                         2169
---------- ---------- ---------- ---------- ---------- ---------- ---------- --------  2219
---------- ---------- ---------- ---------- ---------- ---------- ---------- --------  2213
VPPTNSAAQA AAAAAAAVAA MSHELEGSPV GVGMGGNLPS PYDTSSMYSN AMAAPLANGN PNTGAKQPPS            2327
```

FIG.4D

MANIPULATION OF NON-TERMINALLY DIFFERENTIATED CELLS USING THE NOTCH PATHWAY

This invention was made with government support under grant number NS 26084 awarded by the National Institutes of Health. The government has certain rights in the invention.

1. FIELD OF THE INVENTION

The present invention is directed to methods for the expansion of non-terminally differentiated cells ("precursor cells") using Notch reagents, by maintaining the differentiation state of the cells without inhibiting proliferation ("mitotic activity") such that an expanded population of non-terminally differentiated cells is obtained. The cells are preferably stem or progenitor cells. These expanded cells can be used in cell replacement therapy to repopulate lost cell populations and help in the regeneration of diseased and/or injured tissues. The expanded cell populations can also be made recombinant and used for gene therapy, or can be used to supply functions (e.g., expressed protein products) associated with of a particular precursor cell or its progeny cells.

2. BACKGROUND OF THE INVENTION

The developmental processes that govern the ontogeny of multicellular organisms, including humans, depends on the interplay between signaling pathways, which gradually narrow the developmental potential of cells from the original totipotent stem cell to the terminally differentiated mature cell, which performs a specialized function, such as a heart cell or a nerve cell.

The fertilized egg is the cell from which all other cell lineages derive, i.e., the ultimate stem cell. As development proceeds, early embryonic cells respond to growth and differentiation signals which gradually narrow the cells' developmental potential, until the cells reach developmental maturity, i.e., are terminally differentiated. These terminally differentiated cells have specialized functions and characteristics, and represent the last step in a multi-step process of precursor cell differentiation into a particular cell.

The transition from one step to the next in cell differentiation is governed by specific biochemical mechanisms which gradually control the progression until maturity is reached. It is clear that the differentiation of tissues and cells is a gradual process which follows specific steps until a terminally differentiated state is reached.

Gastrulation, the morphogenic movement of the early embryonic cell mass, results in the formation of three distinct germ cell layers, the ectoderm, the mesoderm, and the endoderm. As cells in each germ cell layer respond to various developmental signals, specific organs are generated which are composed of specific differentiated cells. For example, the epidermis and the nervous system develop from ectoderm-derived cells, the respiratory system and the digestive tract are developed from endoderm-derived cells, and mesoderm-derived cells develop into the connective tissues, the hematopoietic system, the urogenital system, muscle, and parts of most internal organs.

The following is a brief outline of how ectoderm, endoderm and mesoderm are developed and further, how these three dermal layers give rise to the different tissues of the body. For a general review of development see Scott F. Gilbert, 1991, Developmental Biology, 3rd Edition, Sinauer Associates, Inc., Sunderland Mass.

The interaction between the dorsal mesoderm and the overlaying ectoderm initiates organogenesis. In this interaction the chordamesoderm directs the ectoderm above it to form the neural tube which will eventually give rise to the brain and the spinal cord. The differentiation of the neural tube into the various regions of the central nervous system is clear at the gross anatomical level where morphogenetic changes shape specific constrictions and bulges to form the chambers of the brain and the spinal cord. At the cellular level, cell migratory events rearrange various groups of cells. The neuroepithelial cells respond to growth and differentiation signals and eventually differentiate into the numerous types of neurons and supportive (glial) cells. Both neural tube and brain are highly regionalized with each specific region serving distinct functional purposes (see FIG. 1). Each cell in this tissue has specific morphological and biochemical characteristics. Differentiated cells are the last step in a lineage where precursor cells responding to developmental cues progress to a more differentiated state until they reach their terminal differentiation state. For example, ependymal cells which are the integral components of the neural tube lining can give rise to precursors which may differentiate into neurons or glia depending on the developmental cues they will receive (Rakic et al., 1982, Neurosci. Rev. 20:429–611).

The neural crest derives from the ectoderm and is the cell mass from which an extraordinary large and complex number of differentiated cell types are produced. (see Table I), including the peripheral nervous system, pigment cells, adrenal medulla and certain areas of the head cartilage.

TABLE I

| Major Neural Crest Derivatives* | | | | |
| --- | --- | --- | --- | --- |
| Pigment cells | Sensory nervous system | Autonomic nervous system | Skeletal and connective tissue | Skeletal and connective tissue |
| TRUNK CREST (INCLUDING CERVICAL CREST) | | | | |
| Melanocytes | Spinal ganglia | Symphathetic | Mesenchyme of dorsal | Adrenal |
| Xanthophores | Some contributions to | Superior cervical | fin in amphibia | medulla |
| (erythrophores) | vagal (X) root ganglia | ganglion | Walls of aortic | Type I cells |
| Iridophores | | Prevertebral ganglia | arches | of carotid |
| (guanophores) | | Paravertebral ganglia | Connective tissue of | body |
| in dermis | | Adrenal medulla | parathyroid | Parafollicle |
| epidermis | | | | (calcitonin- |
| and epidermal | | Parasympahtetic | | producing) |
| derivates | | Remark's ganglion | | cells of |

TABLE I-continued

| | | Major Neural Crest Derivatives* | | |
|---|---|---|---|---|
| Pigment cells | Sensory nervous system | Autonomic nervous system | Skeletal and connective tissue | Skeletal and connective tissue |
| | | Pelvic plexus | | thyroid |
| | | Visceral and enteric | | |
| | | ganglia | | |
| | | Some supportive cells | | |
| | | Glia (oligodendrocytes) | | |
| | | Schwann sheath cells | | |
| | | Some contribution to | | |
| | | meninges | | |
| | | CRANIAL CREST | | |
| Small, belated contribution | Trigeminal (V) Facial (VII) root Glossopharyngeal (IX) root (superior ganglia) Vagal (X) root (jugular ganglia) | Parasympahtetic ganglia Ciliary Ethmoid Sphenopalatine Submandibular | Most visceral cartilages Trabeculae carneae (ant.) Contributes cells to posterior trabeculae, basal plate, parachordal cartilages Odontoblasts | |
| | | Supportive cells | Head mesenchyme (membrane bones) | |

*Derived from Gilbert, 1991, Developmental Biology, 3rd Edition, Sinauer Associates, Inc., Sunderland MA, p. 182.

The fate of neural crest cells will depend on where they migrate and settle during development since the cells will encounter different differentiation and growth signals that govern their ultimate differentiation. The pluripotentiality of neural crest cells is well established (LeDouarin et al., 1975, Proc. Natl. Acad. Sci USA 72:728–732). A single neural crest cell can differentiate into several different cell types. Transplantation experiments of cell populations or single neural crest cells point to the remarkably plastic differentiation potential of these cells. Even though the cell lineages of the various differentiation pathways have not been established to the degree they have in the hematopoietic development, the existence of multi-potential cell precursors, reminiscent to those seen in the hematopoietic system, is well founded.

The cells covering the embryo after neurulation form the presumptive epidermis. The epidermis consists of several cellular layers which define a differentiation lineage starting from the undifferentiated, mitotically active basal cells to the terminally differentiated non-dividing keratinocytes. The latter cells are eventually shed and constantly replenished by the underlying less differentiated precursors. Psoriasis, a pathogenic condition of the skin results from the exfoliation of abnormally high levels of epidermal cells.

Skin is not only the derivative of epidermis. Interactions between mesenchymal dermis, a tissue of mesodermal origin and the epidermis at specific sites, result in the formation of cutaneous appendages, hair follicles, sweat glands and apocrine glands. The cell ensemble that produces hairs is rather dynamic in that the first embryonic hairs are shed before birth and replaced by new follicles (vellus). Vellus, a short and silky hair, remains on many parts of the body which are considered hairless, e.g., forehead and eye lids. In other areas vellus can give way to "terminal" hair. Terminal hair can revert into the production of unpigmented vellus, a situation found normally in male baldness.

The endoderm is the source of the tissues that line two tubes within the adult body. The digestive tube extends throughout the length of the body. The digestive tube gives rise not only to the digestive tract but also to, for example, the liver, the gallbladder and the pancreas. The second tube, the respiratory tube, forms the lungs and part of the pharynx. The pharynx gives rise to the tonsils, thyroid, thymus, and parathyroid glands.

The genesis of the mesoderm which has also been referred to as the mesengenic process gives rise to a very large number of internal tissues which cover all the organs between the ectodermal wall and the digestive and respiratory tubes. As is the case with all other organs it is the intricate interplay between various intercellular signaling events and the response of non-terminally differentiated precursor cells that will eventually dictate specific cellular identities. To a large degree organ formation depends on the interactions between mesenchymal cells with the adjacent epithelium. The interaction between dermis and epidermis to form, e.g., hairs, has been described above. The formation of the limbs, the gut organs, e.g., liver or pancreas, kidney, teeth, etc., all depend on interactions between specific mesenchymal and epithelial components. In fact, the differentiation of a given epithelium depends on the nature of the adjacent mesenchyme. For example, when lung bud epithelium is cultured alone, no differentiation occurs. However, when lung bud epithelium is cultured with stomach mesenchyme or intestinal mesenchyme, the lung bud epithelium differentiates into gastric glands or villi, respectively. Further, if lung bud epithelium is cultured with liver mesenchyme or bronchial mesenchyme, the epithelium differentiates into hepatic cords or branching bronchial buds, respectively.

2.1. ADULT TISSUES AND PRECURSOR CELLS

Embryonic development produces the fully formed organism. The morphologic, i.e., cellular boundaries of each organ are defined and in the juvenile or adult individual the maintenance of tissues whether during normal life or in response to injury and disease, depends on the replenishing of the organs from precursor cells that are capable of responding to specific developmental signals.

The best known example of adult cell renewal via the differentiation of immature cells is the hematopoietic system. Here, developmentally immature precursors (hematopoietic stem and progenitor cells) respond to molecular signals to gradually form the varied blood and lymphoid cell types.

While the hematopoietic system is the best understood self renewing adult cellular system it is believed that most, perhaps all, adult organs harbor precursor cells that under the right circumstances, can be triggered to replenish the adult tissue. For example, the pluripotentiality of neural crest cells has been described above. The adult gut contains immature precursors which replenish the differentiated tissue. Liver has the capacity to regenerate because it contains hepatic immature precursors; skin renews itself, etc. Through the mesengenic process, most mesodermal derivatives are continuously replenished by the differentiation of precursors. Such repair recapitulates the embryonic lineages and entails differentiation paths which involve pluripotent progenitor cells.

Mesenchymal progenitor cells are pluripotent cells that respond to specific signals and adopt specific lineages. For example, in response to bone morphogenic factors, mesenchymal progenitor cells adopt a bone forming lineage. For example, in response to injury, mesodermal progenitor cells can migrate to the appropriate site, multiply and react to local differentiation factors, consequently adopting a distinct differentiation path. It has been suggested that the reason that only a limited tissue repair is observed in adults is because there are too few progenitor cells which can adopt specific differentiation lineages. It is clear that if such progenitor cells could be expanded, then the tissue repair could be much more efficient. An expanded pool of stem and progenitor cells, as well as non-terminally differentiated cells supplying a desired differentiation phenotype, would be of great value in gene therapy and myriad therapeutic regimens.

2.2. THE NOTCH PATHWAY

Genetic and molecular studies have led to the identification of a group of genes which define distinct elements of the Notch signaling pathway. While the identification of these various elements has come exclusively from Drosophila using genetic tools as the initial guide, subsequent analyses have lead to the identification of homologous proteins in vertebrate species including humans. FIG. 2 depicts the molecular relationships between the known Notch pathway elements as well as their subcellular localization (Artavanis-Tsakonas et al., 1995, Science 268:225–232).

The extracellular domain of Notch carries 36 EGF-like repeats, two of which have been implicated in interactions with the Notch ligands Serrate and Delta. Delta and Serrate are membrane bound ligands with EGF homologous extracellular domains, which interact physically with Notch on adjacent cells to trigger signaling.

Functional analyses involving the expression of truncated forms of the Notch receptor have indicated that receptor activation depends on the six cdc10/ankyrin repeats in the intracellular domain. Deltex and Suppressor of Hairless, whose over-expression results in an apparent activation of the pathway, associate with those repeats.

Deltex is a cytoplasmic protein which contains a ring zinc finger. Suppressor of Hairless on the other hand, is the Drosophila homologue of CBF1, a mammalian DNA binding protein involved in the Epstein-Barr virus-induced immortalization of B cells. It has been demonstrated that, at least in cultured cells, Suppressor of Hairless associates with the cdc10/ankyrin repeats in the cytoplasm and translocates into the nucleus upon the interaction of the Notch receptor with its ligand Delta on adjacent cells (Fortini and Artavanis, 1994, Cell 79:273–282). The association of Hairless, a novel nuclear protein, with Suppressor of Hairless has been documented using the yeast two hybrid system therefore, it is believed that the involvement of Suppressor of Hairless in transcription is modulated by Hairless (Brou et al., 1994, Genes Dev. 8:2491; Knust et al. 1992, Genetics 129:803).

Finally, it is known that Notch signaling results in the activation of at least certain bHLH genes within the Enhancer of split complex (Delidakis et al., 1991, Genetics 129:803). Mastermind encodes a novel ubiquitous nuclear protein whose relationship to Notch signaling remains unclear but is involved in the Notch pathway as shown by genetic analysis (Smoller et al., 1990, Genes Dev. 4:1688).

The generality of the Notch pathway manifests itself at different levels. At the genetic level, many mutations exist which affect the development of a very broad spectrum of cell types in Drosophila. Knockout mutations in mice are embryonic lethals consistent with a fundamental role for Notch function (Swiatek et al., 1994, Genes Dev. 8:707). Mutations in the Notch pathway in the hematopoietic system in humans are associated with lymphoblastic leukemia (Ellison et al., 1991, Cell 66:649–661). Finally the expression of mutant forms of Notch in developing Xenopus embryos interferes profoundly with normal development (Coffman et al., 1993, Cell 73:659).

The expression patterns of Notch in the Drosophila embryo are complex and dynamic. The Notch protein is broadly expressed in the early embryo, and subsequently becomes restricted to uncommitted or proliferative groups of cells as development proceeds. In the adult, expression persists in the regenerating tissues of the ovaries and testes (reviewed in Fortini et al., 1993, Cell 75:1245–1247; Jan et al., 1993, Proc. Natl. Acad. Sci. USA 90:8305–8307; Sternberg, 1993, Curr. Biol. 3:763–765; Greenwald, 1994, Curr. Opin. Genet. Dev. 4:556–562; Artavanis-Tsakonas et al., 1995, Science 268:225–232). Studies of the expression of Notch1, one of three known vertebrate homologues of Notch, in zebrafish and Xenopus, have shown that the general patterns are similar; with Notch expression associated in general with non-terminally differentiated, proliferative cell populations. Tissues with high expression levels include the developing brain, eye and neural tube (Coffman et al., 1990, Science 249:1438–1441; Bierkamp et al., 1993, Mech. Dev. 43:87–100). While studies in mammals have shown the expression of the corresponding Notch homologues to begin later in development, the proteins are expressed in dynamic patterns in tissues undergoing cell fate determination or rapid proliferation (Weinmaster et al., 1991, Development 113:199–205; Reaume et al., 1992, Dev. Biol. 154:377–387; Stifani et al., 1992, Nature Genet. 2:119–127; Weinmaster et al., 1992, Development 116:931–941; Kopan et al., 1993, J. Cell Biol. 121:631–641; Lardelli et al., 1993, Exp. Cell Res. 204:364–372; Lardelli et al., 1994, Mech. Dev. 46:123–136; Henrique et al., 1995, Nature 375:787–790; Horvitz et al., 1991, Nature 351:535–541; Franco del Amo et al., 1992, Development 115:737–744). Among the tissues in which mammalian Notch homologues are first expressed are the pre-somitic mesoderm and the developing neuroepithelium of the embryo. In the pre-somitic mesoderm, expression of Notch1 is seen in all of the migrated mesoderm, and a particularly dense band is seen at the anterior edge of pre-somitic mesoderm. This expression has been shown to decrease once the somites have formed, indicating a role for Notch in the differentiation of somatic precursor cells (Reaume et al., 1992, Dev. Biol. 154:377–387; Horvitz et al., 1991, Nature 351:535–541). Similar expression patterns are seen for mouse Delta (Simske et al., 1995, Nature 375:142–145).

Within the developing mammalian nervous system, expression patterns of Notch homologue have been shown to be prominent in particular regions of the ventricular zone of the spinal cord, as well as in components of the peripheral nervous system, in an overlapping but non-identical pattern. Notch expression in the nervous system appears to be limited to regions of cellular proliferation, and is absent from nearby populations of recently differentiated cells (Weinmster et al., 1991, Development 113:199–205; Reaume et al., 1992, Dev. Biol. 154:377–387; Weinmaster et al., 1992, Development 116:931–941; Kopan et al., 1993, J. Cell Biol. 121:631–641; Lardelli et al., 1993, Exp. Cell Res. 204:364–372; Lardelli et al., 1994, Mech. Dev. 46:123–136; Henrique et al., 1995, Nature 375:787–790; Horvitz et al., 1991, Nature 351:535–541). A rat Notch ligand is also expressed within the developing spinal cord, in distinct bands of the ventricular zone that overlap with the expression domains of the Notch genes. The spatio-temporal expression pattern of this ligand correlates well with the patterns of cells committing to spinal cord neuronal fates, which demonstrates the usefulness of Notch as a marker of populations of cells for neuronal fates (Henrique et al., 1995, Nature 375:787–790). This has also been suggested for vertebrate Delta homologues, whose expression domains also overlap with those of Notch1 (Larsson et al., 1994, Genomics 24:253–258; Fortini et al., 1993, Nature 365:555–557; Simske et al., 1995, Nature 375:142–145). In the cases of the Xenopus and chicken homologues, Delta is actually expressed only in scattered cells within the Notch1 expression domain, as would be expected from the lateral specification model, and these patterns "foreshadow" future patterns of neuronal differentiation (Larsson et al., 1994, Genomics 24:253–258; Fortini et al., 1993, Nature 365:555–557).

Other vertebrate studies of particular interest have focused on the expression of Notch homologues in developing sensory structures, including the retina, hair follicles and tooth buds. In the case of the Xenopus retina, Notch1 is expressed in the undifferentiated cells of the central marginal zone and central retina (Coffman et al., 1990, Science 249:1439–1441; Mango et al., 1991, Nature 352:811–815). Studies in the rat have also demonstrated an association of Notch1 with differentiating cells in the developing retina have been interpreted to suggest that Notch1 plays a role in successive cell fate choices in this tissue (Lyman et al., 1993, Proc. Natl. Acad. Sci. USA 90:10395–10399).

A detailed analysis of mouse Notch1 expression in the regenerating matrix cells of hair follicles was undertaken to examine the potential participation of Notch proteins in epithelial/mesenchymal inductive interactions (Franco del Amo et al., 1992, Development 115:737–744). Such a role had originally been suggested for Notch1 based on the its expression in rat whiskers and tooth buds (Weinmaster et al., 1991, Development 113:199–205). Notch1 expression was instead found to be limited to subsets of non-mitotic, differentiating cells that are not subject to epithelial/mesenchymal interactions, a finding that is consistent with Notch expression elsewhere.

Expression studies of Notch proteins in human tissue and cell lines have also been reported. The aberrant expression of a truncated Notch1 RNA in human T-cell leukemia results from a translocation with a breakpoint in Notch1 (Ellisen et al., 1991, Cell 66:649–661). A study of human Notch1 expression during hematopoiesis has suggested a role for Notch1 in the early differentiation of T-cell precursors (Mango et al., 1994, Development 120:2305–2315). Additional studies of human Notch1 and Notch2 expression have been performed on adult tissue sections including both normal and neoplastic cervical and colon tissue. Notch1 and Notch2 appear to be expressed in overlapping patterns in differentiating populations of cells within squamous epithelia of normal tissues that have been examined and are clearly not expressed in normal columnar epithelia, except in some of the precursor cells. Both proteins are expressed in neoplasias, in cases ranging from relatively benign squamous metaplasias to cancerous invasive adenocarcinomas in which columnar epithelia are replaced by these tumors (Mello et al., 1994, Cell 77:95–106).

Insight into the developmental role and the general nature of Notch signaling has emerged from studies with truncated, constitutively activated forms of Notch in several species. These recombinantly engineered Notch forms, which lack extracellular ligand-binding domains, resemble the naturally occurring oncogenic variants of mammalian Notch proteins and are constitutively activated using phenotypic criteria (Greenwald, 1994, Curr. Opin. Genet. Dev. 4:556; Fortini et al., 1993, Nature 365:555–557; Coffman et al., 1993, Cell 73:659–671; Struhl et al., 1993, Cell 69:1073; Rebay et al., 1993, Genes Dev. 7:1949; Kopan et al., 1994, Development 120:2385; Roehl et al., 1993, Nature 364:632).

Ubiquitous expression of activated Notch in the Drosophila embryo suppresses neuroblast segregation without impairing epidermal differentiation (Struhl et al., 1993, Cell 69:331; Rebay et al., 1993, Genes Dev. 7:1949).

Persistent expression of activated Notch in developing imaginal epithelia likewise results in an overproduction of epidermis at the expense of neural structures (Struhl et al., 1993, Cell 69:331).

Neuroblast segregation occurs in temporal waves that are delayed but not prevented by transient expression of activated Notch in the embryo (Struhl et al., 1993, Cell 69:331).

Transient expression in well-defined cells of the Drosophila eye imaginal disc causes the cells to ignore their normal inductive cues and to adopt alternative cell fates (Fortini et al., 1993, Nature 365:555–557).

Studies utilizing transient expression of activated Notch in either the Drosophila embryo or the eye disc indicate that once Notch signaling activity has subsided, cells may recover and differentiate properly or respond to later developmental cues (Fortini et al., 1993, Nature 365:555–557; Struhl et al., 1993, Cell 69:331).

For a general review on the Notch pathway and Notch signaling, see Artavanis-Tsakonas et al., 1995, Science 268:225–232.

Citation or identification of any reference in Section 2 or any other section of this application shall not be construed as an admission that such reference is available as prior art to the present is invention.

3. SUMMARY OF THE INVENTION

The present invention is directed to methods for the expansion of non-terminally differentiated cells ("precursor cells") by activating the Notch pathway in a precursor cell such that differentiation of the precursor cell is inhibited without destroying the ability of the cell to proliferate. The precursor cell is preferably a stem or progenitor cell. The present invention is also directed to methods for the expansion of precursor cells in precursor cell containing-populations by activating the Notch pathway in the cells such that the differentiation of the stem cell is inhibited without affecting the mitotic activity of the stem cells. Further, the precursor cells can be isolated from a cell population, if desired, before or after Notch pathway activation. Activation of the Notch pathway is preferably achieved by contacting the cell with a Notch ligand, e.g., in soluble form or recombinantly expressed on a cell surface or immobilized on a solid surface, or by introducing into the cell a recombinant nucleic acid expressing a dominant active Notch mutant or an activating Notch ligand, or other molecule that activates the Notch pathway.

Activating Notch in the precursor cell renders the precursor cell refractory to differentiation signals, thus substantially inhibiting differentiation and allowing maintenance of the cell in its differentiation stage, and, optionally, expansion of the cell upon exposure to cell growth conditions. Thus, the methods of the invention provide precursor cells of a specific differentiation state. Thus, in one embodiment, such a cell which expresses a desired differentiation phenotype (e.g., production of a desired hormone or growth factor) can is be administered to a patient wherein the differentiation phenotype is therapeutically useful (e.g., hormone or growth factor deficiency). Alternatively, an expanded stem or progenitor cell population produced by activation of Notch and cell growth can be used to replace or supplement the stem or progenitor cell lineage in a patient by administration of such cell population. If desired, members of the expanded cell population can be induced to differentiate in vitro prior to in vivo administration, so as to supply to the patient the function of a more differentiated cell population. Preferably, the Notch activation is carried out in vitro and is reversible so that upon in vivo administration of the cells differentiation can occur. Thus, for example, in a preferred embodiment, a Notch ligand is used to activate Notch on the cells, e.g., by being added in soluble form to the cell media, or contacting the cells with a layer of cells in culture expressing the Notch ligand (e.g., Delta, Serrate) on its surface.

The precursor cells to be expanded in the present invention can be isolated from a variety of sources using methods known to one skilled in the art (see Section 5.5, infra). The precursor cells can be of any animal, preferably mammalian, most preferably human, and can be of primary tissue, cell lines, etc. The precursor cells can be of ectodermal, mesodermal or endodermal origin. Any precursor cells which can be obtained and maintained in vitro can potentially be used in accordance with the present invention. In a preferred embodiment, the precursor cell is a stem cell. Such stem cells include but are not limited to hematopoietic stem cells (HSC), stem cells of epithelial tissues such as the skin and the lining of the gut, embryonic heart muscle cells, and neural stem cells (Stemple and Anderson, 1992, Cell 71:973–985). The stem cells can be expanded under cell growth conditions, i.e., conditions that promote proliferation ("mitotic activity") of the cells.

The least differentiated cell in a cell lineage is termed a stem cell. However, stem cell is an operational term. The classic definition of the stem cell is a cell which can divide to produce another stem cell (self-renewal capacity), as well as a cell which can differentiate along multiple specific differentiation paths. It is often the case that a particular cell within a differentiation lineage, has derived from a "less" differentiated parent and can still divide and give rise to a "more" differentiated cellular progeny. FIG. 3 describes diagrammatically hematopoietic development. Totipotent, pluripotent and progenitor stem cells are referred to in the figure.

A "precursor cell" may or may not divide and can be triggered to adopt a different differentiation state but not necessarily a fully differentiated state, by responding to specific developmental signals.

The present invention is also directed to methods for use of the expanded precursor cells for use in gene therapy as well as for use in providing desired cell populations, e.g., for regenerating injured and/or diseased tissues. The expanded precursor cell populations can be administered to a patient using methods commonly known to those skilled in the art (see Section 5.8, infra). In other specific embodiments, after Notch activation and expansion, the precursor can be induced to differentiate in vivo, or alternatively in vitro, followed by administration to an individual, to provide a differentiated phenotype to a patient. Additionally, Notch activation and expansion can be carried out in vitro subsequent to in vitro production of a precursor cell of a desired phenotype from a stem or progenitor cell.

The present invention is also directed to precursor cells containing recombinant genes, such that the gene is inheritable and expressible by the precursor cell or its progeny. These recombinant precursor cells can be transplanted into a patient such that the desired gene is expressed in the patient to alleviate a disease state caused by the lack of or deficient expression of the recombinant gene. The precursor cells can be made recombinant either before or after precursor cell expansion. Methods of tranfecting the nucleic acid encoding the desired gene product such that the precursor cell or its progeny stably expresses the gene product are known to those of skill in the art and are described infra.

4. BRIEF DESCRIPTION OF THE FIGURES

FIG. 1 is a diagram showing regional specialization during human brain development. (Gilbert, 1991, Developmental Biology, 3rd Edition, Sinauer Associates, Inc., Sunderland Mass., p. 166.)

FIG. 2 is a schematic diagram of the Notch signaling pathway. The Notch receptor can bind to either Delta or Serrate through its extracellular domain. Ligand binding can result in receptor multimerization that is stabilized by interactions between the intracellular ankyrin repeats of Notch and the cytoplasmic protein Deltex. These events can control the nuclear translocation of the DNA-binding protein Suppressor of Hairless and its known association with the Hairless protein. The transcriptional induction of the Enhancer of Split bHLH genes appears to depend on Notch signaling.

FIGS. 4A–4D show the highly conserved ankyrin repeat region of Notch , hum N (SEQ ID NO.:1), Tan-1 (SEQ ID NO.:2), Xen N (SEQ ID NO.:3), Dros N (SEQ ID NO.:4).

FIGS. 5A–F. Expression of activated Notch and neural differentiation in cone cell precursors of transgenic flies bearing both sev-Notch$^{nuc1}$ and the activated Raf construct sE-raf$^{tor¥9}$. Third-instar larval eye imaginal discs were reacted with mouse monoclonal antibody C17.9C6 directed against the intracellular domain of Notch and rat monoclonal antibody 7E8A10 directed against the neural antigen ELAV and visualized with immunofluorescent secondary antibodies using confocal microscopy. Low (5A–C) and high (5E–F) magnification images of posterior eye disc regions showing nuclear Notch staining (green) in sevenless-expressing cells (5A,D), nuclei expressing ELAV (red)

undergoing neural differentiation (5B,E) and corresponding image overlays of both staining patterns (5C,F). The field shown in (5A–C) spans ommatidial rows 10–23, with the posterior margin of the disc visible at the left: nuclei that express Notch protein do not express ELAV. Individual cone cell precursor nuclei of similar developmental ages are labeled 'N' in (5D) if they stain for Notch but not ELAV, and are labelled 'E' in (5E) if they stain for ELAV but not Notch. Faint ELAV staining (red) was often observed beneath strongly Notch-positive (green) cone cell precursor nuclei; examples are indicated by asterisks in (5E). Optical sectioning revealed that this ELAV staining corresponds to R1,3, 4, 6 and 7 photoreceptor cell precursor nuclei that are located immediately below and partially intercalated with the cone cell precursor nuclei. Identical staining patterns were observed for sev-Notch$^{nucl}$ flies bearing the activated Sevenless tyrosine kinase construct sev-S11 or the activated Ras1 construct sevRas1$^{Va112}$ instead of sE-$^{torY9}$ (data not shown).

Figure 6A:
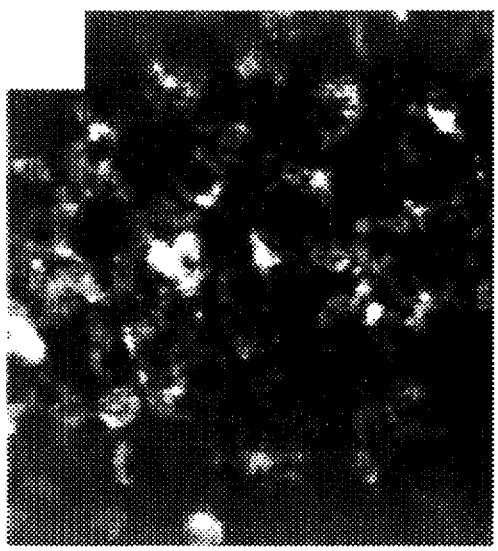
Figure 6B:
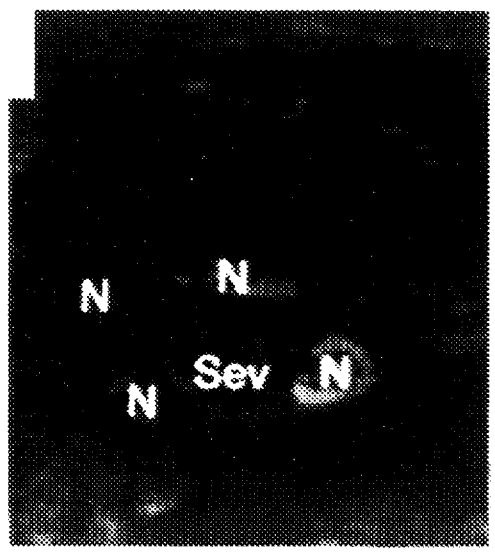

FIGS. 6A–B. Co-expression of activated Notch and activated Sevenless proteins in cone cell precursors of sevenless$^{d2}$ flies bearing sev-Notch$^{nucl}$ and sev-S11. Third-instar larval eye imaginal discs were reacted with rat polyclonal antibody Rat5 directed against the intracellular domain of Notch and mouse monoclonal antibody sev150C3 directed against the 60 kD subunit of Sevenless and visualized with immunofluorescent secondary antibodies using confocal microscopy. The sevenless$^{d2}$ allele produces no protein recognized by mAb sev150C3. (6A) Image overlay of two horizontal optical sections collected at slightly different apical levels within the same posterior eye disc quadrant, showing expression of activated Notch (green) in most of the cone cell precursor nuclei and expression of activated Sevenless (purple) in most of the corresponding apical membranes of the cone cell precursor population. The ring-shaped distribution of Sevenless protein in each assembling ommatidium represents the apical microvillar tufts of up to four cone cell precursors and the R7 precursor cell. (6B) Higher magnification image overlay similar to that in (6A), showing a developing ommatidium in which all four cone cell precursor nuclei express Notch (labelled 'N') and all or most cone cell precursor apical membrane tufts exhibit strong Sevenless expression (labelled 'Sev').

Figure 7:
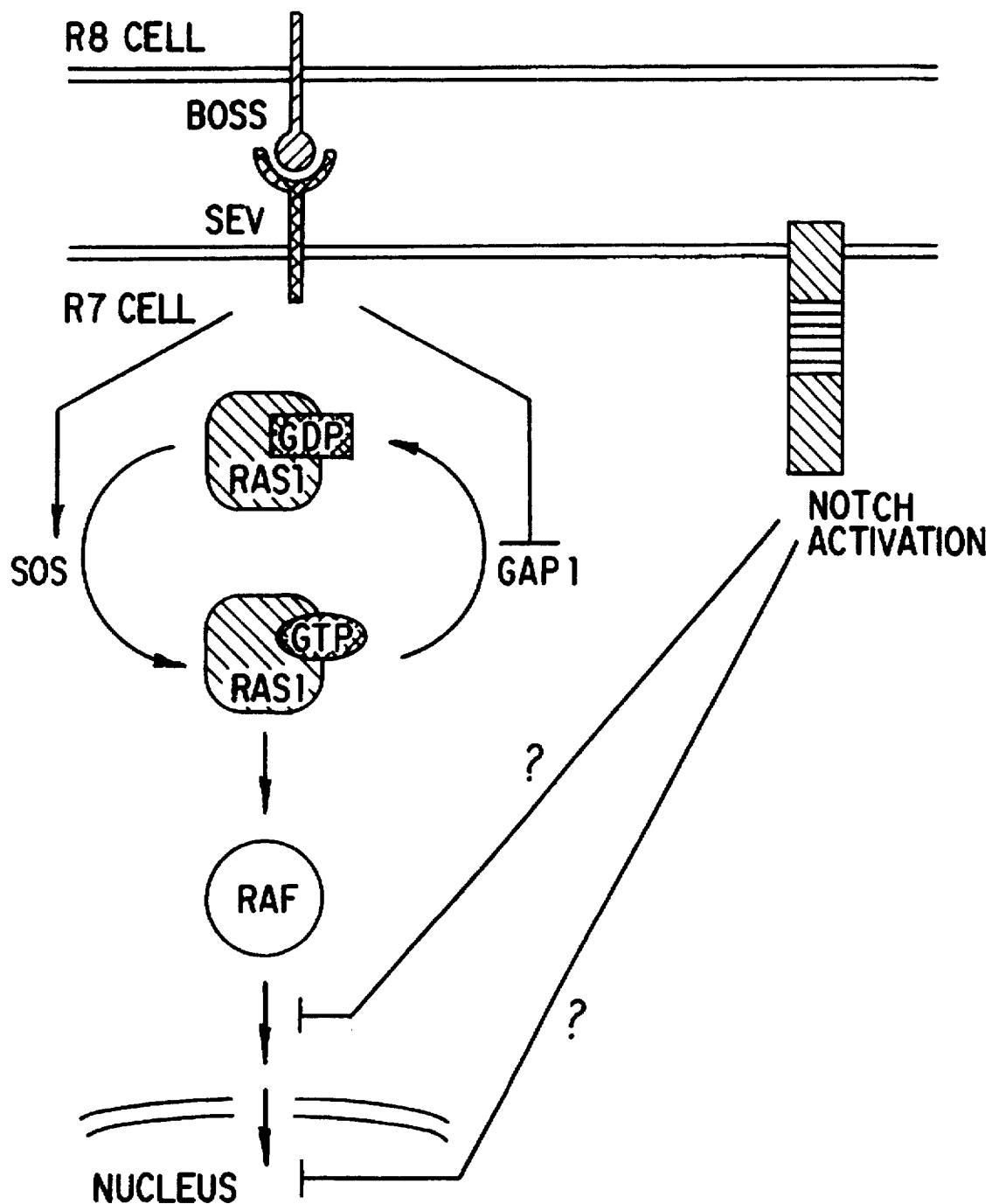

FIG. 7. Schematic representation of the epistatic relationship between Notch activation and the signalling pathway involving the sevenless receptor tyrosine kinase, Ras1 and Raf during neural induction of the R7 cell precursor in Drosophila. Sevenless protein (Sev) in the R7 cell precursor is activated by binding to its ligand Bride of sevenless (Boss), presented by the adjacent R8 cell, resulting in Ras1 activation presumably via regulation of the activities of its guanine nucleotide exchange factor Son-of-sevenless and its GTPase-activating protein Gap1. Ras1 activation leads to the activation of Raf. This signalling pathway is inhibited by Notch activation at some point downstream of Raf.

5. DETAILED DESCRIPTION OF THE INVENTION

The present invention is directed to methods for the expansion of non-terminally differentiated cells ("precursor cells") by activating the Notch pathway in a precursor cell such that the differentiation of the precursor cell is inhibited without destroying the ability of the cell to proliferate. As used herein, "precursor cells" shall mean any non-terminally differentiated cells. The precursor cell is preferably a stem or progenitor cell. The present invention is also directed to methods for the expansion of precursor cells in precursor cell containing-populations by activating the Notch pathway in the cells such that the differentiation of the stem cell is inhibited without affecting the mitotic activity of the cells. Further, the precursor cells can be isolated from a cell population, if desired, before or after Notch pathway activation. Activation of Notch pathway is preferably achieved by contacting the cell with a Notch ligand, e.g., in soluble form or recombinantly expressed on a cell surface or immobilized on a solid surface, or by introducing into the cell a recombinant nucleic acid expressing a dominant active Notch mutant or an activating Notch ligand, or other molecule that activates the Notch pathway.

Agonists of the Notch pathway are able to activate the Notch pathway at the level of protein-protein interaction or protein-DNA interaction. Agonists of Notch include but are not limited to proteins and derivatives comprising the portions of toporythmic proteins such as Delta or Serrate or Jagged (Lindsell et a., 1995, Cell 80:909–917) that mediate binding to Notch, and nucleic acids encoding the foregoing (which can be administered to express their encoded products in vivo). In a preferred embodiment, the agonist is a protein or derivative or fragment thereof comprising a functionally active fragment such as a fragment of a Notch ligand that mediates binding to a Notch protein. In another preferred embodiment, the agonist is a human protein or portion thereof (e.g., human Delta). In another preferred embodiment the agonist is Deltex or Suppressor of Hairless or a nucleic acid encoding the foregoing (which can be administered to express its encoded product in vivo).

The Notch pathway is a signal transducing pathway comprising elements which interact, genetically and/or molecularly, with the Notch receptor protein. For example, elements which interact with the Notch protein on both a molecular and genetic basis are, for example, and not by way of limitation, Delta, Serrate and Deltex. Elements which interact with the Notch protein genetically are, for example, and not by way of limitation, Mastermind, Hairless and Suppressor of Hairless.

Activating Notch function in the precursor cell renders the precursor cell refractory to differentiation signals, thus substantially inhibiting differentiation and allowing maintenance of the cell in its differentiation stage, and, optionally, expansion of the cell upon exposure to cell growth conditions. Thus, the methods of the invention provide precursor cells of a specific differentiation state. Thus, in one embodiment, such a cell which expresses a desired differentiation phenotype (e.g., production of a desired hormone or growth factor) can be administered to a patient wherein the differentiation phenotype is therapeutically useful (e.g., hormone or growth factor deficiency). Alternatively, an expanded stem or progenitor cell population produced by activation of Notch and cell growth can be used to replace or supplement the stem or progenitor cell lineage in a patient by administration of such cell population. If desired, members of the expanded cell population can be induced to differentiate in vitro prior to in vivo administration, so as to supply to the patient the function of a more differentiated cell population. Preferably, the Notch activation is carried out in vitro and is reversible so that upon in vivo administration of the cells differentiation can occur. Thus, for example, in a preferred embodiment, a Notch ligand is used to activate Notch on the cells, e.g., by being added in soluble form to the cell media, or contacting the cells with a layer of cells in culture expressing the Notch ligand (e.g., Delta, Serrate) on its surface.

The precursor cells to be expanded in the present invention can be isolated from a variety of sources using methods known to one skilled in the art (see Section 5.5, infra). The precursor cells can be of ectodermal, mesodermal or endodermal origin. Any precursor cells which can be obtained and maintained in vitro can potentially be used in accordance with the present invention. In a preferred embodiment, the precursor cell is a stem cell. Such stem cells include but are not limited to hematopoietic stem cells (HSC), stem cells of epithelial tissues such as the skin and the lining of the gut, embryonic heart muscle cells, and neural stem cells (Stemple and Anderson, 1992, Cell 71:973–985). The stem cells can be expanded under cell growth conditions, i.e., conditions that promote proliferation ("mitotic activity") of the cells.

Figure 1:
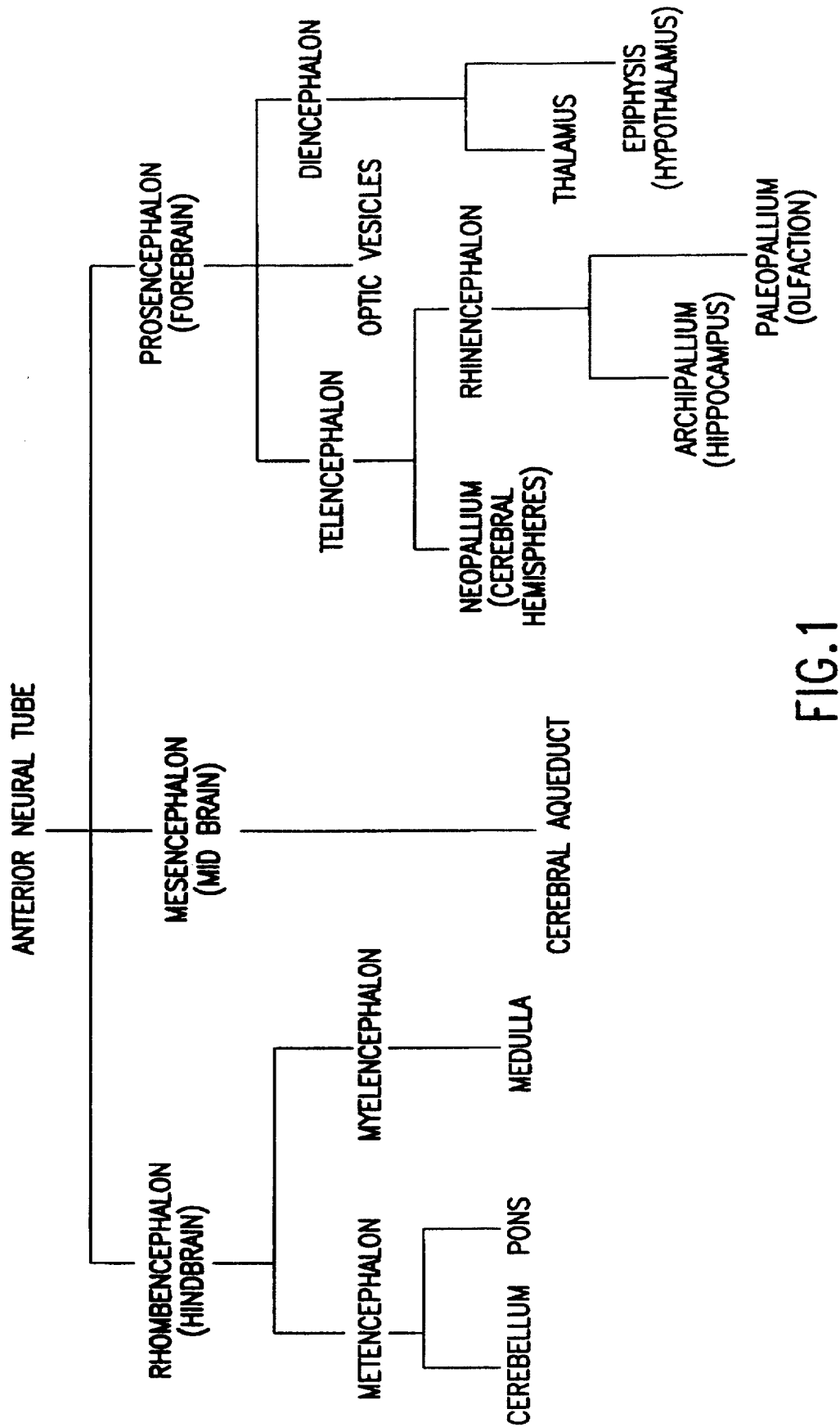
Figure 2:
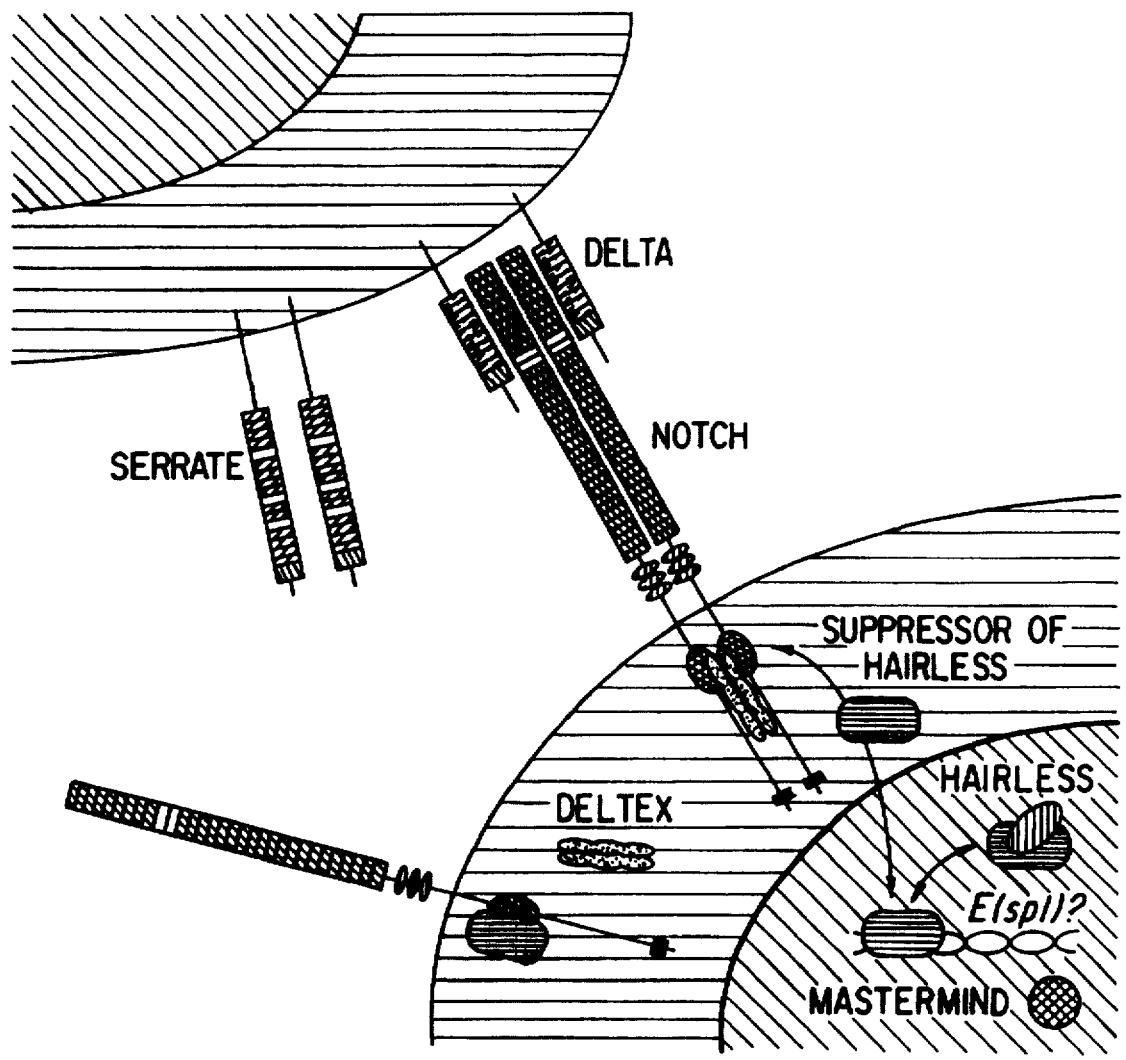
Figure 3:
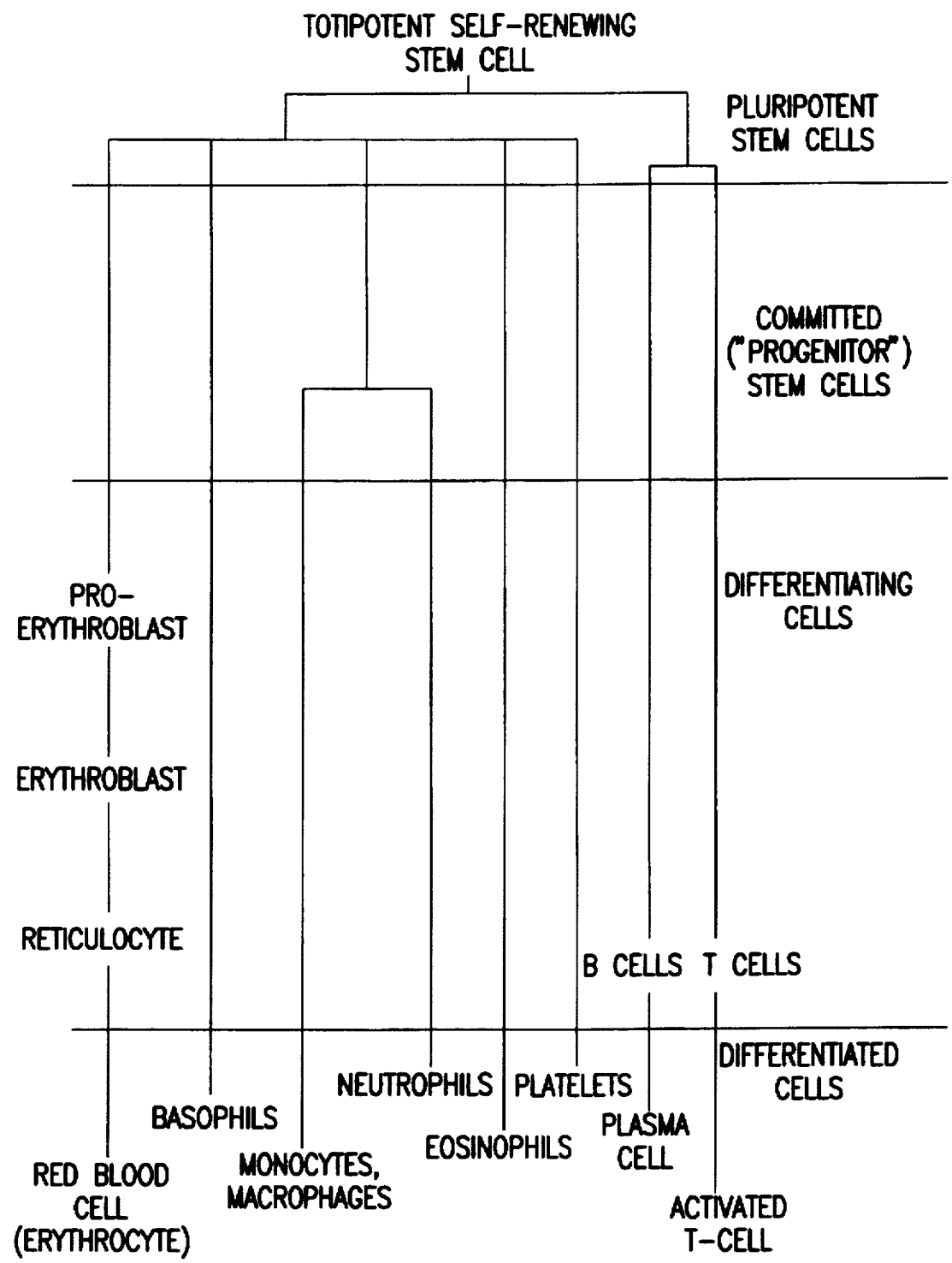
FIG. 3 is a schematic diagram of the origin of mammalian blood and lymphoid cells. (Gilbert, 1991, Developmental Biology, 3rd Edition, Sinauer Associates, Inc., Sunderland Mass., p. 232).
Figure 5A:
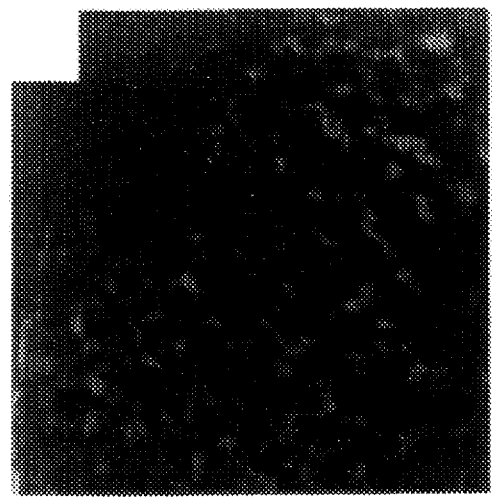
Figure 5B:
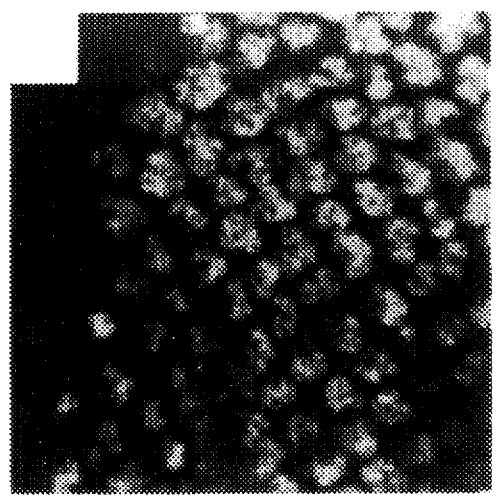
Figure 5C:
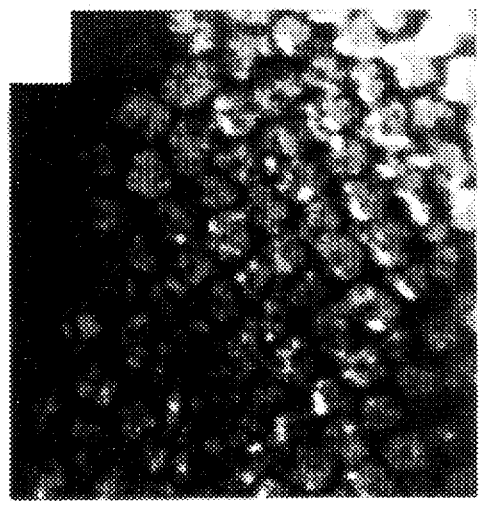
Figure 5D:
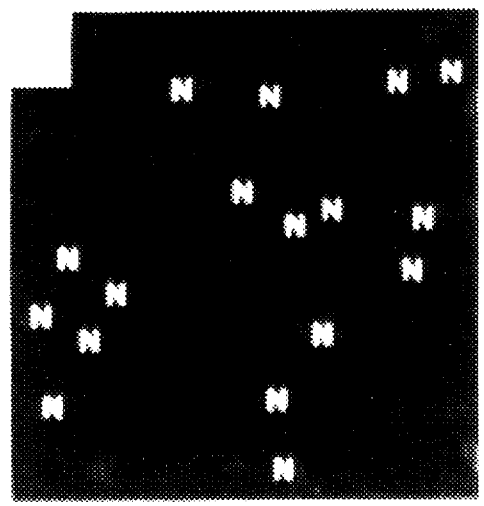
Figure 5E:
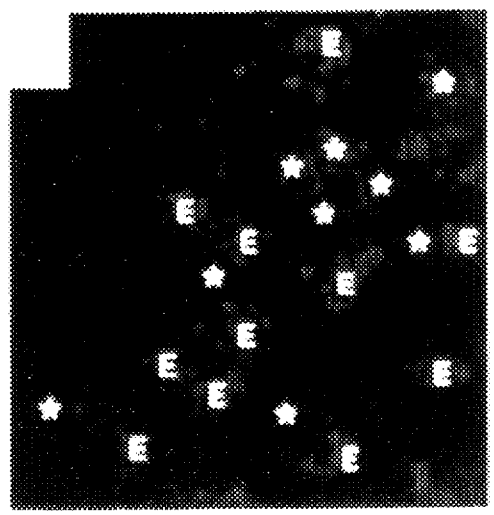
Figure 5F:
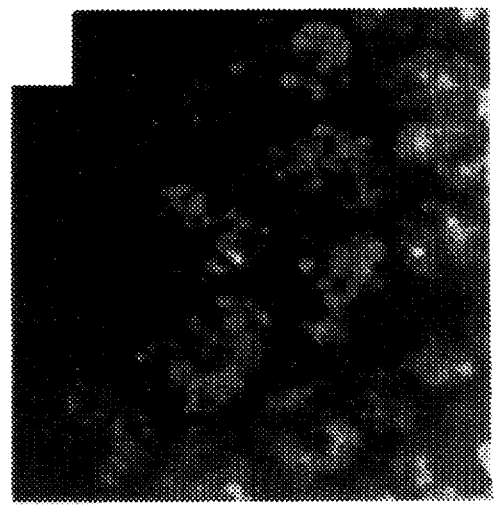

The least differentiated cell in a cell lineage is termed a stem cell. However, stem cell is an operational term. The classic definition of the stem cell is a cell which can divide to produce another stem cell (self-renewal capacity), as well as a cell which can differentiate along multiple specific differentiation paths. It is often the case that a particular cell within a differentiation lineage, has derived from a "less" differentiated parent and can still divide and give rise to a "more" differentiated cellular progeny. FIG. 3 describes diagrammatically hematopoietic development. Totipotent, pluripotent and progenitor stem cells are referred to in the figure.

A "precursor cell" has specific biochemical properties, may or may not divide and can be triggered to adopt a different differentiation state but not necessarily a fully differentiated state, by responding to specific developmental signals.

The present invention is also directed to methods for use of the expanded precursor cells for use in gene therapy as well as for use in providing desired cell populations and for use in regenerating injured and/or diseased tissues. The expanded precursor cell populations can be administered to a patient using methods commonly known to those skilled in the art (see Section 5.8, infra). In other specific embodiments, after Notch activation and expansion, the precursor cell can be induced to differentiate in vivo, or alternatively in vitro, followed by administration to an individual, to provide a differentiated phenotype to a patient. Additionally, Notch activation and expansion can be carried out in vitro subsequent to in vitro production of a precursor cell of a desired phenotype from a stem or progenitor cell.

The present invention is also directed to precursor cells expressing recombinant genes, such that the precursor cells express a desired gene. These recombinant precursor cells can be transplanted into a patient such that the desired gene is expressed in the patient to alleviate a disease state caused by the lack of expression of the recombinant gene. The precursor cells can be made recombinant either before or after precursor cell expansion. Methods of tranfecting the nucleic acid encoding the desired gene product such that the precursor cell or its progeny stably expresses the gene product are known to those of skill in the art and are described infra.

The subject into which the expanded cells or their progeny are introduced, or from which precursor cells can be derived, is preferably an animal, including but not limited to animals such as cows, pigs, horses, chickens, cats, dogs, etc., and is preferably a mammal, and most preferably human.

In an embodiment of the present invention, the subjects to which the cells are administered are immunocompromised or immunosuppressed or have an immune deficiency. For example, the subject has Acquired Immune Deficiency Syndrome or has been exposed to radiation or chemotherapy regimens for the treatment of cancer, and the subjects are administered hematopoietic or immune precursor cells such that the administered cells perform a needed immune or hematopoietic function.

Preferably, the expanded precursor cell is originally derived from the subject to which it is administered, i.e., the transplant is autologous.

For clarity of disclosure, and by way of limitation, the detailed description of the invention is divided into the following sub-sections:

(i) Notch signaling and stem cell differentiation.
(ii) Notch activation inhibits the differentiation of stem cells.
(iii) Activation of the Notch pathway.
(iv) Notch and terminal differentiation.
(v) Obtaining precursor cells.
(vi) Gene therapy.
(vii) Pharmaceutical compositions.
(viii) Transplantation.

5.1. NOTCH SIGNALING AND STEM CELL DIFFERENTIATION

The progression of a precursor cell to a more mature or differentiated state depends on a combination of signals that ultimately govern the differentiation steps. Specific factors, for example, bone morphogenic factors or the various factors known to be important in hematopoiesis, for example, interleukin-5 or thrombopoietin, together with intercellular and cell-extracellular matrix interactions contribute to the differentiation of a precursor cell along a specific differentiation path.

The effectors of such contributions are the various signaling pathways which transmit the extracellular signal to the nucleus, ultimately changing transcriptional expression patterns, i.e., genes expressed only in the tissue that is the cells' ultimate fate are switched on and conversely others are switched off, such that, e.g., kidney cells express kidney-specific genes and do not express liver cell-specific proteins. In order for a precursor cell to respond to the various extracellular signals, it must be competent to do so, for example, in order to respond to a soluble factor the cell must express a receptor which can recognize the factor. Tissue competence has been articulated in the classic studies of Waddington, 1940, Organisers and Genes, Cambridge University Press, Cambridge, England.

The present invention is based, at least in part, on the discovery that the Notch signaling pathway is not a pathway that transmits specific developmental signals such that cell differentiation is effected, but rather it controls the competence of a precursor cell to interpret and respond to differentiation signals. The Notch pathway is a general and evolutionarily conserved developmental "switch." Specifically, when the Notch pathway is activated in precursor cells, the precursor cells are unable to respond to particular differentiation signals but generally the mitotic ability of the precursor cells remains (i.e., the cells can proliferate). The existence of the Notch pathway allows for the manipulation of the differentiation state of precursor cells without knowing all of the differentiation signals, e.g., growth factors, which are required for the maintenance of a particular differentiation state or for advancing the cell to a more differentiated state. In a preferred aspect, the inhibitory effect on differentiation by activating the Notch pathway with a Notch function agonist can be reversed by adding an antagonist of the Notch pathway or diluting out the Notch pathway agonist.

5.2. NOTCH ACTIVATION INHIBITS THE DIFFERENTIATION OF PRECURSOR CELLS

Notch regulates the competence of many different cell types to respond to more specific signals, with the particular cell fates chosen depending upon the developmental history of each cell type and the specific signaling pathways operating within it. When Notch function is activated in a precursor cell (e.g., progenitor or stem cell), the precursor cell can be prevented from differentiating even in the presence of the correct differentiation signals. Once, however, Notch function activation subsides, the cells can respond again to developmental cues. We have shown, using human keratinocytes which have been transfected with activated forms of Notch, that while cells stably expressing activated Notch forms are prevented from differentiating, their proliferation potential is not affected.

The modulation of Notch pathway activity offers a novel and unique tool to manipulate the fate of precursor cells. A precursor at a given developmental state can be "frozen" into that state by virtue of activating the Notch pathway. Importantly, these cells may be expanded, since Notch signaling activity may not destroy or, preferably, does not substantially impair, their ability to divide. Thus, precursor cells may be expanded, ex vivo in order to provide a source of precursors which are useful in gene therapy as well as tissue repair. Notch agonists are also useful in cases where it is important to maintain a cell in a particular differentiation state in order to provide indefinitely, or for a given period of time, a chemical produced by a cell of that differentiated state, to a particular tissue. In this latter embodiment, for example, it may be desired to activate Notch in the cells administered in vivo for a long period of time (e.g., hours or days) or substantially irreversibly, e.g., by excapsulating the cells with a soluble Notch agonist, or having them recombinantly express a Notch dominant active mutant from a constitutive promoter, respectively.

An embodiment of the present invention is to treat the desired cell population with agonists of the Notch pathway and then either allow these cells to proliferate in culture before transplanting them back into the appropriate region, or directly transplanting them without necessarily allowing them to proliferate in vitro. Antagonists can be used to reverse or neutralize the action of the Notch function agonist. For example, and not by way of limitation, a Notch ligand or a molecule that mimics the ligand can be used to keep Notch receptor expressing cells in an "activated" state while withdrawal of the ligand will reverse that effect.

It is possible in many cases that the simple activation of Notch may not suffice to expand the stem cells ex vivo. Subjecting the cell to growth conditions, e.g., culturing it in the presence of specific growth factors or combinations of growth factors may be necessary, nevertheless, the importance of Notch pathway activation in these events will be essential since the presence of only those factors will generally not be sufficient to maintain those cells in culture without differentiation occurring.

5.3. ACTIVATION OF NOTCH FUNCTION

An agonist of Notch function is an agent that promotes activation of Notch function. As used herein, "Notch function" shall mean a function mediated by the Notch signaling pathway.

Notch function activation is preferably carried out by contacting a precursor cell with a Notch function agonist. The agonist of Notch function can be a soluble molecule, recombinantly expressed as a cell-surface molecule, on a cell monolayer with which the precursor cells are contacted, a molecule immobilized on a solid phase. In another embodiment, the Notch agonist can be recombinantly expressed from a nucleic acid introduced into the precursor cells. Notch function agonists of the present invention include Notch proteins and analogs and derivatives (including fragments) thereof; proteins that are other elements of the Notch pathway and analogs and derivatives (including fragments) thereof; antibodies thereto and fragments or other derivatives of such antibodies containing the binding region thereof; nucleic acids encoding the proteins and derivatives or analogs; as well as toporythmic proteins and derivatives and analogs thereof which bind to or otherwise interact with Notch proteins or other proteins in the Notch pathway such that Notch function is promoted. Such agonists include but are not limited to Notch proteins and derivatives thereof comprising the intracellular domain, Notch nucleic acids encoding the foregoing, and proteins comprising toporythmic protein domains that interact with Notch (e.g., the extracellular domain of Delta, Serrate or Jagged). Other agonists include Deltex and Suppressor of Hairless. These proteins, fragments and derivatives thereof can be recombinantly expressed and isolated or can be chemically synthesized.

In a preferred embodiment the agonist is a protein consisting of at least a fragment (termed herein "adhesive fragment") of the proteins encoded by toporythmic genes which mediate binding to Notch proteins or adhesive fragments thereof. Toporythmic genes, as used herein, shall mean the genes Notch, Delta, Serrate, Jagged, Suppressor of Hairless and Deltex, as well as other members of the Delta/Serrate/Jagged family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in Drosophila).

Vertebrate homologs of Notch pathway elements have been cloned and sequenced. For example, these include Serrate (Lindsell et al., 1995, Cell 80:909–917); Delta (Chitnis et al., 1995, Nature 375:761; Henrique et al., 1995, Nature 375:787–790; Bettenhausen et al., 1995, Development 121:2407); and Notch (Coffman et al., 1990, Science 249:1438–1441; Bierkamp et al., 1993, Mech. Dev. 43:87–100; Stifani et al., 1992, Nature Genet. 2:119–127; Lardelli et al., 1993, Exp. Cell Res. 204:364–372; Lardelli et al., 1994, Mech. Dev. 46:123–136; Larsson et al., 1994, Genomics 24:253–258; Ellisen et al., 1991, Cell 66:649–661; Weinmaster et al., 1991, Development 113:199–205; Reaume et al., 1992, Dev. Biol. 154:377–387; Weinmster et al., 1992, Development 116:931–941; Franco del Amo et al., 1993, Genomics 15:259–264; and Kopan et al., 1993, J. Cell. Biol. 121:631–641).

In one embodiment, the Notch agonist is expressed from a recombinant nucleic acid. For example, in vivo expression of truncated, "activated" forms of the Notch receptor lacking the extra cellular, ligand binding domain results in gain of function mutant phenotypes. When analyzed at the single cell level, these phenotypes demonstrate that expression of such molecules in progenitor or stem cells, prevents the cells from responding to differentiation signals, thus inhibiting differentiation. It has also been mentioned that this process may be desired to be reversible, since when the activated Notch receptor is no longer expressed the undifferentiated stem cells can respond to differentiation signals and differentiate. Thus, preferably the Notch dominant active mutant is expressed inside the precursor cells from an inducible promoter, such that expression can be induced In vitro for expansion, with the inducer lacking in vivo so that differentiation occurs after administration of the transplanted cells.

Alternatively, in another embodiment the agonist of Notch function is not a recombinant dominant Notch active mutant.

Alternatively, in another embodiment, contacting of the precursor cells with a Notch agonist is not done by incubation with other cells recombinantly expressing a Notch ligand on the cell surface (although in other embodiments, this method can be used).

In another embodiment, the recombinantly expressed Notch agonist is a chimeric Notch protein which comprises the intracellular domain of Notch and the extracellular domain of another ligand-binding surface receptor. For example, a chimeric Notch protein comprising the EGF receptor extracellular domain and the Notch intracellular domain is expressed in a precursor cell. However, the Notch pathway will not be active unless the EGF receptor ligand EGF is contacted with the precursor cell-expressing the chimera. As with the inducible promoter controlling the expression of the truncated form of Notch, the activity of the chimeric Notch protein is reversible; when EGF is removed from the cells, Notch activity will cease and the cell can then differentiate. Notch activity can again be turned on with the addition of the ligand.

A systematic deletion analysis of the intracellular domain of Notch demonstrates that the Notch sequences that are both necessary and sufficient for the downstream signaling of the Notch receptor are confined to the ankyrin repeats of the intracellular region (Matsuno et al., 1995, Development 121:2633-2644 and unpublished results). Using the yeast two hybrid system it was discovered that the ankyrin repeats interact homotypically.

Expression of appropriate deletion constructs in the defined cellular environment of the developing Drosophila eye demonstrates that expression of a polypeptide fragment comprising just the ankyrin repeats resulted in an activated phenotype. Not surprisingly this is the part of the Notch protein which is most highly conserved among various species. FIGS. 4A–4D show the high sequence homology of ankyrin repeats across evolution.

These findings suggest that any small molecules, for example, but not by way of limitation, polypeptides or antibodies which bind to the Notch ankyrin repeats, can block its function, and hence behave as antagonists of the pathway. Conversely, molecules that mimic the Notch ankyrin repeat activity can behave as agonists of the Notch pathway. Since the expression of truncated forms of Notch give mutant phenotypes in the developing Drosophila eye, genetic screens for modifiers of these phenotypes can be used for identifying and isolating additional gene products that can act as agonists or antagonists of the pathway.

Genes that act as enhancers of the activated phenotypes are potential agonists and those that act as suppressors are potential antagonists.

Deltex and Suppressor of Hairless are also agonists of Notch function that can be used. It has been shown that the activation of the Notch pathway, as judged by the induction of activated phenotypes similar to those induced by the expression of activated forms of Notch, can be achieved by manipulating the expression of Deltex (Schweisguth and Posakony, 1994, Development 120:1477), as well as Suppressor of Hairless (Matsuno et al., 1995, Development 121:2633) both of which can interact with the ankyrin repeats of Notch.

Using the yeast 'interaction trap' assay (Zervos et al., 1993, Cell 72:223-232), as well as cell culture co-localization studies, the protein regions responsible for heterotypic interactions between Deltex and the intracellular domain of Notch, as well as homotypic interaction among Deltex molecules were defined. The function of the Deltex-Notch interaction domains was examined by in vivo expression studies. Taken together, data from over-expression of Deltex fragments and from studies of physical interactions between Deltex and Notch demonstrate that Deltex positively regulates the Notch pathway through interactions with the Notch ankyrin repeats.

Experiments involving cell cultures indicate that the Deltex-Notch interaction prevents the cytoplasmic retention of Suppressor of Hairless protein, which is normally sequestered in the cytoplasm via association with the Notch ankyrin repeats and translocates to the nucleus when Notch binds to its ligand, Delta. On the basis of these findings Deltex appears to regulate Notch activity by antagonizing the interaction between Notch and Suppressor of Hairless. The translocation of the normally cytoplasmic Suppressor of Hairless protein to the nucleus when Notch binds to a ligand (Fortini and Artavanis-Tsakonas, 1994, Cell 79:273-282) is a convenient assay to monitor for Notch function as well as for the ability of Notch agonists of the present invention to activate Notch function.

Suppressor of Hairless has been shown to be a DNA binding protein. Genetic and molecular data indicate that the activity of Suppressor of Hairless can be influenced by its binding to the nuclear protein Hairless. Moreover it appears that the transcription of at least some of the bHLH genes of the Enhancer of split complex depends directly on Notch signaling and the ability of Suppressor of Hairless to recognize the appropriate binding sites upstream of these genes. Manipulation of these various interactions (e.g., disrupting the interaction between Notch and Suppressor of Hairless with an antibody directed against the ankyrin repeats) will result in modulating the activity of the Notch pathway.

Finally, the Notch pathway can be manipulated by the binding of Notch ligands (e.g., Delta, Serrate) to the extracellular portion of the Notch receptor. Notch signaling appears to be triggered by the physical interaction between the extracellular domains of Notch and its membrane-bound ligands on adjacent cells. The expression of full length ligands on one cell triggers the activation of the pathway in the neighboring cell which expresses the Notch receptor. Not surprisingly, the ligands act as agonists of the pathway. On the other hand, the expression of truncated Delta or Serrate molecules which lack intracellular domains expressed in neighboring cells results in non-autonomous, dominant negative phenotypes. This demonstrates that these mutant forms of the receptor act as antagonists of the pathway.

The definition of the various molecular interactions among the Notch pathway elements provides additional specific pharmacological targets and assays which can be used to screen for Notch function agonists and antagonists. Having evaluated the consequences of a particular molecular manipulation in vivo, this information can be used to design biochemical in vitro screening assays for biological or pharmaceuticals that interfere or enhance Notch function.

Screening for molecules that will trigger the dissociation of the Notch ankyrin repeats with Suppressor of Hairless and the subsequent translocation of Suppressor of Hairless from the cytoplasm to the nucleus results in the identification of agonists. The activation of transcription of a reporter gene which has been engineered to carry several Suppressor of Hairless binding sites at its 5' end in a cell that expresses Notch also results in the identification of agonists of the pathway.

Reversing the underlying logic of these assays leads to the identification of antagonists. For example, cell lines expressing the aforementioned reporter gene can be treated with chemicals and biologicals and those which have the capacity to stop the expression of the reporter gene can be identified.

The precursor cell in which Notch function has been activated is subjected to cell growth conditions to induce proliferation. Such cell growth conditions (e.g., cell culture medium, temperature, if growth is done in vitro) can be any of those commonly known in the art. Preferably, both Notch activation and exposure to cell growth conditions is carried out in vitro. Contacting the cell with a Notch function agonist and exposing the cell to cell growth conditions can be carried out concurrently or, if the agonist acts over a sufficient period of time, sequentially (as long as Notch function activation to inhibit differentiation is present while cell growth occurs).

5.3.1. MODULATING OTHER SIGNALING PATHWAYS WITH NOTCH

Notch defines a general cell interaction mechanism whose biological function is to permit or block the action of developmental signals that are essential for the progression of undifferentiated progenitor cells to a more differentiated state. Consistent with that is the discovery that one can modulate the activity of other signaling pathways by modulating Notch. Thus, in another embodiment, the invention provides methods of modulating other cell signal transduction pathway, e.g., those that mediate cell growth and differentiation.

A dramatic example of how Notch signaling regulates specific differentiation pathways involves the Ras pathway in the developing Drosophila eye, which is used to transmit an inductive signal generated by ligand-induced activation of the Sevenless receptor tyrosine kinase, and is blocked by appropriately timed activation of the Notch pathway. We have demonstrated that in the cone cell precursors of the developing Drosophila eye, Notch activation and Ras1-mediated signalling separately cause opposite cell-fate alterations. Co-expression studies in these cells demonstrate that Notch activation inhibits the neural differentiation produced by constitutively activated components of a well-defined inductive signalling cascade, including the Sevenless receptor tyrosine kinase, Ras1 and Raf. Therefore, the activation of Notch in a cell blocks the action of activated ras (see Section 6, infra).

Consistent with the notion that Notch activation initiates a distinct signalling pathway that modulates the cellular response to signals transduced by diverse pathways is the finding that the modulation of Notch activity controls the action of Drosophila wingless (Hing et al., 1994, Mech. Dev. 47:261–268), a homologue of the mouse wnt-1 locus, which encodes a secreted protein involved in cell-signaling during various stages in development (Nusslein-Volhard and Wieschaus, 1980, Nature 287:795–801; Martinez Arias et al., 1988, Development 103:157–170; Nusse and Varmus, 1992, Cell 69:1073–1087; Struhl and Basler, 1993, Cell 72:527–540). Therefore, agonists and antagonists of the Notch pathway provide a novel and unique tool in manipulating the activity of specific signals which control the differentiation of cells using pathways unrelated to Notch. In a particular embodiment of the invention, cells are contacted with an agonist of Notch function to inhibit the function of a signaling pathway that regulates cell growth or differentiation.

5.4. NOTCH AND TERMINAL DIFFERENTIATION

The present invention is also directed to using agents to inhibit the Notch pathway such that cells, which are maintained in one differentiation state by Notch pathway activity, can be allowed to change their differentiation state. Notch expression is generally associated with non-terminally differentiated cells. One exception to this general rule is that Notch is expressed in post-mitotic neurons of rat and human adult retina (Ahmad et al., unpublished results). Immunocytochemical staining data indicates that the Notch polypeptides recognized by the antibodies are nuclear. The expression of engineered Notch fragments that are localized in the nuclear has been documented (reviewed in Artavanis-Tsakonas et al., 1995, Science 268:225–232), and these fragments were shown to be associated with activated mutant phenotypes. The presence of an activated form of Notch in the nucleus may lock these cells into a particular state of differentiation by restricting or completely blocking their capacity to respond to differentiation and/or proliferation stimuli. Therefore, it is conceivable that these post-mitotic neurons maintain their differentiated state by virtue of an activated Notch-1 form that is independent of Notch ligands. This state may perhaps afford such cell populations a certain plasticity. For example, an eventual cessation of nuclear Notch-1 activity might allow these cells to re-enter a mitotic state and/or respond to specific differentiation signals. In this context, it is interesting to note that retinal neurons in lower vertebrates such as Goldfish and Xenopus have regenerative capacity. Chemical ablation of specific neurons, such as degeneration of dopaminergic amacrine cells by 6-OH dopamine result in their replacement by regeneration (Reh and Tully, 1986, Dev. Biol. 114(2) :463–469). However, such plasticity for regenerative purposes have not been observed in higher vertebrates. The observed Notch-1 activity in mature retinal neurons in the rat may represent the recapitulation of the functional significance of Notch-1 in retinal regeneration in lower vertebrates. The invention thus provides a method comprising antagonizing Notch function to confer regenerative properties on the mammalian neurons (e.g., of the central nervous system), thus leading to regeneration. Such a method comprises contacting a mammalian neuron with an antagonist of Notch function and exposing the neuron to neuronal cell growth conditions.

5.5. OBTAINING PRECURSOR CELLS

Precursor cells can be obtained by any method known in the art. The cells can be obtained directly from tissues of an individual or from cell lines or by production in vitro from less differentiated precursor cells, e.g., stem or progenitor cells. An example of obtaining precursor cells from less differentiated cells is described in Gilbert, 1991, Developmental Biology, 3rd Edition, Sinauer Associates, Inc., Sunderland Mass. Briefly, progenitor cells can be incubated in the presence of other tissues or growth and differentiation factors which cause the cell to differentiate. For example, when lung bud epithelium is cultured alone, no differentiation occurs. However, when lung bud epithelium is cultured with stomach mesenchyme or intestinal mesenchyme, the lung bud epithelium differentiates into gastric glands or villi, respectively. Further, if lung bud epithelium is cultured with liver mesenchyme or bronchial mesenchyme, the epithelium differentiates into hepatic cords or branching bronchial buds, respectively. Once a progenitor cell has reached a desired differentiation state, a Notch function agonist can be used to stop differentiation.

5.5.1. ISOLATION OF STEM OR PROGENITOR CELLS

The following describes approaches which allow for the isolation of precursor cells and precursor cell-containing tissues, which are to be treated with agonists and, if subsequently desired, antagonists of the Notch pathway according to the present invention. As already alluded to, isolated cell types or even mixtures of cell populations can be treated with Notch function agonists. The isolated precursor cell or precursor cell population can be cultured ex vivo for proliferation which under the influence of the Notch function agonists and cell growth conditions can continue to divide, i.e., expand, in order to reach the desired numbers before transplantation. Optionally, a recombinant gene can be introduced into the cell so that it or its progeny expresses a desired gene product before transplantation. Introduction of a recombinant gene can be accomplished either before or after precursor cell expansion.

In a preferred embodiment, the precursor cell populations are purified or at least highly enriched. However, in order to treat precursor cells with Notch reagents it is not necessary that the precursor cells are a pure population. Once a mixture is treated, only Notch pathway-expressing non-differentiated precursors will be refractory to differentiation signals but will respond to growth signals while their differentiated partners will eventually terminally differentiate and cease growing, such that the precursor cells will outgrow the differentiated cells and can be purified from the original mixed population. Consequently, the precursor population can still be expanded selectively. Furthermore, purification may not be necessary or desirable prior to therapeutic administration in vivo.

The isolation of precursor cells for use in the present invention can be carried out by any of numerous methods commonly known to those skilled in the art. For example, one common method for isolating precursor cells is to collect a population of cells from a patient and using differential antibody binding, wherein cells of one or more certain differentiation stages are bound by antibodies to differentiation antigens, fluorescence activated cell sorting is used to separate the desired precursor cells expressing selected differentiation antigens from the population of isolated cells. The following section describes exemplary methods for the isolation of various types of stem cells.

5.5.1.1. MESENCHYMAL STEM CELLS

One of the most important type of progenitor cells vis a vis for therapeutic applications are those derived from the mesenchyme. Mesenchymal progenitors give rise to a very large number of distinct tissues (Caplan, 1991, J. Orth. Res 641–650). Most work to date involves the isolation and culture of cells which can differentiate into chondrocytes and osteoblasts. The systems developed to isolate the relevant progenitor cell populations were worked out first in chick embryos (Caplan, 1970, Exp. Cell. Res. 62:341–355; Caplan, 1981, 39th Annual Symposium of the Society for Developmental Biology, pp. 37–68; Caplan et al., 1980, Dilatation of the Uterine Cervix 79–98; DeLuca et al., 1977, J. Biol. Chem. 252:6600–6608; Osdoby et al., 1979, Dev. Biol. 73:84–102; Syftestad et al., 1985, Dev. Biol. 110:275–283). Conditions were defined under which chick mesenchymal cells differentiated into chondrocytes and bone. Id. With regard to cartilage and bone, the properties of mouse or human mesenchymal limb appear to be quite similar if not identical (Caplan, 1991, J. Orth. Res. 641–650). Mesenchymal cells capable of differentiating into bone and cartilage have also been isolated from marrow (Caplan, 1991, J. Orth. Res. 641–650).

Caplan et al., 1993, U.S. Pat. No. 5,226,914 describes an exemplary method for isolating mesenchymal stem cells from bone marrow. These isolated marrow stem cells can be used in conjunction with Notch reagents to expand the stem cell population. These expanded cells may then be transplanted into a host where they can differentiate into osteocytes, cartilage, chondrocytes, adipocytes, etc., depending on the surrounding microenvironment of the transplant site.

Animal models involving mice, rats as well as avian preparations, have suggested that the source for mesenchymal stem cells is bone marrow. It has been possible to purify marrow mesenchymal cells by their differential adhesion to culture dishes and demonstrate that they can differentiate, e.g., into osteoblasts. Expansion of such isolated stem cells using Notch reagents can provide a source of cells which when transplanted to the appropriate sites will be induced by the microenvironment to differentiate into the appropriate lineage and help repair damaged and/or diseased tissue. It is expected that the animal models described to date will be applicable to humans. Indeed, as far as cartilage and bone are concerned, the properties of mouse and human limb mesenchymal cells in culture are quite similar, if not identical (Hauska, 1974, Dev. Biol. 37:345–368; Owens and Solursh, 1981, Dev. Biol. 88:297–311). The isolation of human marrow and the demonstration that cells deriving from it can sustain osteogenesis has been described, e.g., by Bab et al., 1988, Bone Mineral 4:373–386.

Several bone marrow isolation protocols have been reported and can be used to obtain progenitor or precursor cells. Single cell suspensions from rat bone marrow can be prepared according to Goshima et al., 1991, Clin. Orth. and Rel. Res. 262:298–311. Human stem cell cultures from marrow can be prepared as described by Bab et al., 1988, Bone Mineral 4:373–386 as follows: Whole marrow cells are obtained from five patients. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described previously (Bab et al., 1984, Calcif. Tissue Int. 36:77–82; Ashton et al., 1984, Calcif. Tissue Int. 36:83–86) by drawing the preparation into a syringe and expelling it several times sequentially through 19, 21, 23 and 25 gauge needles. The cells are counted using a fixed volume hemocytometer and the concentration adjusted to $1-5 \times 10^8$ total marrow cells per ml suspension. Positive and negative control cell suspensions can be set as described before (Shteyer et al., 1986, Calcif. Tissue Int. 39:49–54), using rabbit whole marrow and spleen cells, respectively.

5.5.1.2. NEURAL STEM CELLS

It is generally assumed that neurogenesis in the central nervous system ceases before or soon after birth. In recent years, several studies have presented evidence indicating that at least to some degree new neurons continue to be added to the brain of adult vertebrates (Alvarez-Buylla and Lois, 1995, Stem Cells (Dayt) 13:263–272). The precursors are generally located in the wall of the brain ventricles. It is thought that from these proliferative regions, neuronal precursors migrate towards target positions where the microenvironment induces them to differentiate. Studies have been reported where cells from the sub-ventricular zone can generate neurons both in vivo as well as in vitro, reviewed in Alvarez-Buylla and Lois, 1995, Stem Cells (Dayt) 13:263–272.

The neuronal precursors from the adult brain can be used as a source of cells for neuronal transplantation (Alvarez-Buylla, 1993, Proc. Natl. Acad. Sci. USA 90:2074–2077). Neural crest cells have also been long recognized to be pluripotent neuronal cells which can migrate and differentiate into different cell neuronal cell types according to the instructions they receive from the microenvironment they find themselves in (LeDouarin and Ziller, 1993, Curr. Opin. Cell Biol. 5:1036–1043).

5.5.1.3. FETAL CELLS

The fact that fetal brain tissue has been shown to have clear behavioral effects when transplanted into adult lesioned brains, has focused attention on human fetal tissue as a potential cell source in transplantation protocols designed to improve neurodegenerative disorders (Bjorklund, 1993, Nature 362:414–415; McKay, 1991, Trends Neurosci. 14:338–340). Nevertheless both ethical, as well as practical considerations make fetal tissue a difficult source to deal with. Expansion of neuronal stem cells whether fetal or otherwise using Notch function agonists provides an alternative source for obtaining the desired quantities of precursor cells for transplantation purposes. Fetal tissues or adult tissues containing precursors can be treated with Notch function agonists as described earlier in order to expand the undifferentiated progenitor cell populations. Fetal cells can placed into primary culture using, for example, protocols developed by Sabate et al., 1995, Nature Gen. 9:256–260, before being treated with Notch function agonists. By way of example but not limitation, the procedure is as follows: Primary cultures of human fetal brain cells can be isolated from human fetuses, obtained from legal abortions after 5 to 12 weeks of gestation. Expulsion can be done by syringe-driven gentle aspiration under echographic control. Fetuses collected in sterile hibernation medium are dissected in a sterile hood under a stereomicroscope. Brains are first removed in toto in hibernation medium containing penicillin G 500 U/ml, streptomycin 100 μg/ml, and fungizon 5 μg/ml. For fetuses of six to eight weeks of age the brain is separated into an anterior (telencephalic vesicles and diencephalon) and a posterior fraction (mesencephalon, pons and cerebellar enlage) and a posterior in toto after careful removal of meninges. For older fetuses, striatal hippocampal, cortical and cerebellar zones expected to contain proliferative precursor cells are visualized under the stereomicroscope and dissected separately. Cells are transferred to either Opti-MEM (Gibco BRL) containing 15% heat-inactivated fetal bovine serum (FBS) (Seromed), or to a defined serum-free medium (DS-FM) with human recombinant bFGF (10 ng/ml, Boehringer), which is a minor modification of the Bottenstein-Sato medium 39 with glucose, 6 g/l, glutamine 2 mM (Gibco BRL), insulin 25 ug/ml (Sigma) transferrin 100 μg/ml (Sigma), sodium selenite 30 nM (Gibco BRL), progesterone 20 nM (Sigma), putrescine 60 nM (Sigma), penicillin G (500 U/ml), streptomycin 100 μg/ml, and fungizon 5 μg/ml. Cells, approximately 40,000 per $cm^2$, are grown at 37° C. in an atmosphere containing 10% $CO_2$ in tissue culture dishes (Falcon or Nunc) coated with gelatin (0.25% wt/vol) followed by Matrigel (Gibco BRL, a basement membrane extract enriched in laminin and containing trace amounts of growth factors diluted one in 20). Cells in culture can be treated with Notch function agonists in order to expand the population of the appropriate cells until the desired cell mass is reached for transplantation.

5.5.1.4. HEMATOPOIETIC STEM CELLS

Any technique which provides for the isolation, propagation, and maintenance in vitro of hematopoietic stem cells (HSC) can be used in this embodiment of the invention. Techniques by which this can be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

Another technique for the isolation of HSC is described by Milner et al., 1994, Blood 83:2057–2062. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that $CD34^+$ hematopoietic stem cells, including the immature subset that lacks expression of individual lineage associated antigens, $CD34^+lin^-$, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for hematopoietic stem cells are also known in the art (e.g., spleen focus forming assays, assays that detect the ability to form progenitors after replating).

5.5.1.5. EPITHELIAL STEM CELLS

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of precursor cells within the germinal layer, the layer closest to the basal lamina. Precursor cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

5.5.1.6. LIVER STEM CELLS

Liver stem cells can be isolated by methods described in PCT Publication WO 94/08598, dated Apr. 28, 1994.

5.5.1.7. KIDNEY STEM CELLS

Mammalian kidney emerges from the metanephric mesenchyme which induces the uteric bud to undergo a series of morphogenetic movements ultimately forming the mature urinary collecting system (Nigam and Brenner, 1992, Curr. Opin. Nephrol. Huper 1:187–191. The uteric bud, an epithelial outgrowth of the Wolfian duct, contracts and induces condensing adjacent mesenchyme along differentiation pathways of epithelial divergence in early embryonic life. Attempts to study this process in vitro have been reported; metanephros in organ culture can be induced to form tubules using embryonic spinal cord as the inducer. While the specific transducing agents that lead to the induction of metanephric mesenchyme by the uteric bud in vivo or by spinal cord in vitro are not known, it is clear that differentiation program is induced in progenitor cells (Karp et al., 1994, Dev.

Biol. 91:5286–5290).

5.5.2. EXPANSION AND DIFFERENTIATION

After the precursors cells have been isolated according to the methods described above or other methods known in the art, the precursor cells can be contacted with an amount of an agonist of Notch function effective to inhibit differentiation, and are exposed to cell growth conditions (e.g., promoting mitosis) such that the cell proliferates to obtain an expanded precursor population according to the present invention.

In one embodiment, substantially no differentiation of the precursor cells occurs during expansion. The amount of differentiation that occurs can be assayed for by known assays, e.g., those that detect the presence of more differentiated cells by detecting functions associated with a particular stage of differentiation, e.g., expression of differentiation antigens on the cell surface or secretion of proteins associated with a particular state, or ability to generate various cell types, or detecting morphology associated with particular stages of differentiation.

Once the population has reached a desired titer, the Notch function agonist can be removed (e.g., by separation, dilution), or a Notch function antagonist can be added, such that Notch function is absent or inhibited allowing at least some of the cells in the expanded population to differentiate in the presence of the desired differentiation signals to a desired differentiation state or to a differentiation state of the cell such that the cell expresses a desired phenotype. Optionally, once the cells reach the desired differentiation state the Notch pathway can again be activated with a Notch agonist to freeze the cell in that differentiation state. The cells can be differentiated to a terminally differentiated state if the function of that terminally differentiated cell is desired.

5.6. GENE THERAPY

The cells produced by manipulation of the Notch pathway can be made recombinant and used in gene therapy. In its broadest sense, gene therapy refers to therapy performed by the administration of a nucleic acid to a subject. The nucleic acid, either directly or indirectly via its encoded protein, mediates a therapeutic effect in the subject. The present invention provides methods of gene therapy wherein a nucleic acid encoding a protein of therapeutic value (preferably to humans) is introduced into the precursor cells expanded according to the invention, before or after expansion, such that the nucleic acid is expressible by the precursor cells and/or their progeny, followed by administration of the recombinant cells to a subject.

The recombinant precursor cells of the present invention can be used in any of the methods for gene therapy available in the art. Thus, the nucleic acid introduced into the cells may encode any desired protein, e.g., a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant precursor cells are used in gene therapy, a gene whose expression is desired in a patient is introduced into the precursor cells such that it is expressible by the cells and/or their progeny, and the recombinant cells are then administered in vivo for therapeutic effect.

Precursor cells or expanded precursor cells can be used in any appropriate method of gene therapy, as would be recognized by those in the art upon considering this disclosure. The resulting action of a recombinant precursor cell or its progeny cells administered to a patient can, for example, lead to the activation or inhibition of a pre-selected gene in the patient, thus leading to improvement of the diseased condition afflicting the patient.

The desired gene is transferred to precursor cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those precursor cells are then delivered to a patient.

In this embodiment, the desired gene is introduced into a precursor cell prior to administration in vivo of the resulting recombinant cell. Such introduction can be carried out by any method known in the art, including but not limited to transfection, electroporation, microinjection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther.

29:69–92) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny.

One common method of practicing gene therapy is by making use of retroviral vectors (see Miller et al., 1993, Meth. Enzymol. 217:581–599). A retroviral vector is a retrovirus that has been modified to incorporate a preselected gene in order to effect the expression of that gene. It has been found that many of the naturally occurring DNA sequences of retroviruses are dispensable in retroviral vectors. Only a small subset of the naturally occurring DNA sequences of retroviruses is necessary. In general, a retroviral vector must contain all of the cis-acting sequences necessary for the packaging and integration of the viral genome. These cis-acting sequences are:

a) a long terminal repeat (LTR), or portions thereof, at each end of the vector;

b) primer binding sites for negative and positive strand DNA synthesis; and c) a packaging signal, necessary for the incorporation of genomic RNA into virions.

The gene to be used in gene therapy is cloned into the vector, which facilitates delivery of the gene into a precursor cell by infection or delivery of the vector into the cell.

More detail about retroviral vectors can be found in Boesen et al., 1994, Biotherapy 6:291–302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are also of use in gene therapy. Adenoviruses are especially attractive vehicles for delivering genes to respiratory precursor cells. Adenoviruses can also be used to deliver genes to precursor cells from the liver, the central nervous system, endothelium, and muscle. Adenoviruses have the advantage of being capable of infecting non-dividing cells. Kozarsky and Wilson, 1993, Current Opinion in Genetics and Development 3:499–503 present a review of adenovirus-based gene therapy. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

It has been proposed that adeno-associated virus (AAV) be used in gene therapy (Walsh et al., 1993, Proc. Soc. Exp. Biol. Med. 204:289–300).

A desired gene can be introduced intracellularly and incorporated within host precursor cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, the desired gene recombinantly expressed in the precursor cell to be introduced for purposes of gene therapy comprises an inducible promoter operably linked to the coding region, such that expression of the recombinant gene is controllable by controlling the presence or absence of the appropriate inducer of transcription.

In another embodiment, if a greater number of differentiated cells is desired before administering to a patient then the precursor cells can be differentiated prior to expansion. In another embodiment, one can expand and differentiate the precursor cells simultaneously such that greater numbers of differentiated cells are obtained.

5.7. PHARMACEUTICAL COMPOSITIONS

The invention provides methods of treatment by administration to a subject of a pharmaceutical (therapeutic) composition comprising a therapeutically effective amount of a recombinant or non-recombinant cell, preferably a stem or progenitor cell. Such a stem cell or recombinant stem cell envisioned for therapeutic use is referred to hereinafter as a "Therapeutic" or "Therapeutic of the invention." In a preferred aspect, the Therapeutic is substantially purified. The subject is preferably an animal, including but not limited to animals such as cows, pigs, horses, chickens, cats, dogs, etc., and is preferably a mammal, and most preferably human.

The present invention provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, or emulsion.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

5.8. TRANSPLANTATION

The expanded stem cell populations of the present invention whether recombinantly expressing a desired gene or not can be transplanted into a patient for the treatment of disease or injury or for gene therapy by any method known in the art which is appropriate for the type of stem cells being transplanted and the transplant site. Hematopoietic stem cells can be transplanted intravenously, as can liver stem cells which will locate to the liver. Neural stem cells can be transplanted directly into the brain at the site of injury or disease.

Methods of introduction include but are not limited to intradermal, intramuscular, intraperitoneal, intravenous, subcutaneous, intranasal, and epidural routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the Therapeutics of the invention locally to the area in need of treatment; this may be achieved by, for example, and not by way of limitation, local infusion during surgery, topical application, e.g., in conjunction with a wound dressing after surgery, by injection, by means of a catheter, or by means of an implant, said implant being of a porous, non-porous, or gelatinous material, including membranes, such as sialastic membranes, or fibers.

The following describes exemplary methods which can be modified for the transplantation of precursor cells: Protocols for the isolation and transplantation of fetal tissues in humans have been reported and clinical trials involving these studies having been carried out. For example, Lindvall et al., 1990, Science 247:574–577, have described results regarding grafts and survival of fetal dopamine neurons after transplantation into brain. Rinsing and partial dissociation of precursor cells, if necessary, can be carried out by a modification of that described in Lindvall et al., 1989, Arch. Neurol. 46:615.

By way of example, implantation of cells into the brain can be performed as follows. Implantation is done at three sites in the left putamen with a stereotactic technique (Lindvall et al., 1989, Arch. Neurol. 46:615). For each site, 20 µl of the dissociated cells is drawn into the instrument (outer diameter, 1.0 mm). The cells are injected along a 10, 12 and 14 mm linear tract, respectively, in either 2.5 µl portions for 15 to 20 seconds each. Between each injection there is a 2 minute delay, and the cannula is then retracted 1.5 to 1.7 mm. After the final injection, the cannula is left in situ for 8 minutes before being slowly withdrawn from the brain. After surgery the cell viability is assessed following the procedure of Brundin et al., 1985, Brain. Res. 331:251.

Another example is outlined by Caplan et al., 1993, U.S. Pat. No. 5,226,914. Briefly, after marrow cells are harvested from bone marrow plugs and the marrow mesenchymal, stem cells are separated by centrifugation. The stem cells are isolated further by selective adherence to the plastic or glass surface of a tissue culture dish. The stem cells are allowed to proliferate but not differentiate. Porous ceramic cubes composed of 60% hydroxyapatite and 40% β-tricalcium phosphate are added to the cells under a slight vacuum. The cubes with adhered cells are implanted into incisional pockets along the backs of nude mice. The mesenchymal stem cells differentiate into bone.

The titer of stem cells transplanted or the amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

6. INHIBITION OF RAS-1-MEDIATED SIGNALING BY ACTIVATED NOTCH IN DROSOPHILA EYE

In the cone cell precursors of the developing Drosophila eye, Notch activation and Ras1-mediated signaling separately cause opposite cell-fate alterations. Co-expression studies in these cells demonstrate that Notch activation inhibits the neural differentiation produced by constitutively activated components of a well-defined inductive signaling cascade, including the Sevenless receptor tyrosine kinase, Ras1 and Raf.

The sevenless signaling pathway is required only for the induction of the R7 photoreceptor cell by the previously determined R8 cell of each ommatidium. The interaction of the sevenless gene product and its ligand, encoded by the bride of sevenless (boss) gene, normally occurs only between two particular cell types during a narrow developmental time window (Basler and Hafen, 1989, Development 107:723–731; Mullins and Rubin, 1991, Proc. Natl. Acad. Sci. USA 88:9387–9391; Krämer et al., 1991, Nature 352:207–212). Flies mutant for either or both genes display a very specific phenotype: misrouting of the R7 cell precursor into the cone-cell fate (Tomlinson and Ready, 1986, Science 231:400–402, 1987, Dev. Biol. 123:264–275; Reinke and Zipursky, 1988, Cell 55:321–330). Within each ommatidium, sevenless is expressed in a small set of cells separated by no more than a few cell diameters, consisting of the R3, R4, and R7 precursor cells, the four cone cell precursor cells, and up to two so-called 'mystery cells' (Tomlinson et al., 1987, Cell 51:143–150; Bowtell et al., 1989, Proc. Natl. Acad. Sci. USA 86:6245–6249; Basler et al., 1989, EMBO J. 8:2381–2386). In wild-type flies, only the R7 precursor cell ever comes into contact with the R8 cell, which is the only eye disc cell type that expresses bride of sevenless, resulting in the recruitment of one R7 cell per ommatidium (Krämer et al., 1991, Nature 352:207–212). Experiments in which sev and boss were expressed ubiquitously under heat-shock gene control have demonstrated that the spatially restricted presentation of ligand by the R8 cell is a crucial feature of this inductive signalling mechanism (Basler and Hafen, 1989, Science 243:931–934; Bowtell et al., 1989, Cell 56:931–936; Van Vactor et al., 1991, Cell 67:1145–1155). Recent studies have shown that activation of the Sevenless receptor tyrosine kinase initiates a signaling cascade involving the activation of Ras1 and the subsequent activation of Raf (Simon et al., 1991, Cell 67:701–716; Bonfini et al., 1992, Science 255:603–606; Dickson et al., 1992, Genes Dev. 6:2327–2339; Dickson et al., Nature 360:600–603). Ras1 and Raf are also downstream targets of other receptor tyrosine kinases in Drosophila, including the torso kinase and the Drosophila EGF receptor homolog (Ambrosio et al., 1989, Nature 342:288–291; Simon et al., 1991, Cell 67:701–716; Doyle and Bishop, 1993, Genes Dev. 7:633–646; Melnick et al., 1993, Development 118:127–138; Diaz-Benjumea and Hafen, 1994, Development 120:569–578).

In contrast to sevenless-mediated signalling, the signalling mechanism involving Notch appears to regulate a common step in cell-fate commitment throughout development. The Drosophila Notch gene encodes a large transmembrane receptor protein with an extracellular domain consisting of 36 tandem EGF-like repeats and 3 Notch/lin-12 repeats as well as an intracellular domain containing 6 tandem cdc10/ankyrin repeats (Wharton et al., 1985, Cell 43:567–581; Kidd et al., 1986, Mol. Cell. Biol. 6:3094–3108). Unlike the sev and boss gene products, the Drosophila Notch protein is widely expressed in developing tissues, including all or most cells of the imaginal eye disc (Johansen et al., 1989, J. Cell Biol. 109:2427–2440; Kidd et al., 1989, Genes Dev. 3:1113–1129; Fehon et al., 1991, J. Cell. Biol. 113:657–669). Analysis of Notch gene mutant phenotypes has revealed that Notch function is required for numerous developmental processes, including embryonic neurogenesis (Poulson, 1937, Proc. Natl. Acad. Sci. USA 23:133–137, 1940, J. Exp. Zool. 83:271–325), mesoderm differentiation (Corbin et al., 1991, Cell 67:311–323), axonal pathfinding (Giniger et al., 1993, Development 117:431–440), oogenesis (Ruohola et al., 1991, Cell 66:433–449; Xu et al., 1992, Development 115:913–922; Cummings and Cronmiller, 1994, Development 120:381–394), and differentiation of adult peripheral nervous system structures (Cagan and Ready, 1989, Genes Dev. 3:1099–1112; Palka et al., 1990, Development 109:167–175; Hartenstein and Posakony, 1990, Dev. Biol. 142:13–30; Hartenstein et al., 1992, Development 116:1203–1220). A detailed study of the phenotypic effects of the conditional loss-of-function allele Notch$^{ts1}$ has shown that every cell type of the adult eye, including the R7 cell, requires Notch activity at some stage for its proper cell-fate specification (Cagan and Ready, 1989, Genes Dev. 3:1099–1112).

In the absence of boss gene function, the sevenless-expressing cells of each ommatidium may be induced to differentiate as neurons by ectopic activation of the Sevenless protein, Ras1, or Raf (Basler et al., 1991, Cell 64:1069–1081; Fortini et al., 1992, Nature 355:559–561; Dickson et al., 1992, Genes Dev. 6:2327–2339; Dickson et al., Nature 360:600–603). Evidence is presented below that the neural induction of these cells by activated sevenless pathway components is blocked by constitutive Notch activation in the developing eye imaginal disc. These results indicate that the signal mediated by Notch and its ligands are integrated with the cell type-specific inductive signal mediated by Sevenless at a point downstream of Raf during R7 photoreceptor cell fate specification. Since both Ras1 and Raf are utilized by other tissue-specific inductive signalling pathways, our data implies that Notch may exert regulatory effects on these pathways as well.

6.1. MATERIALS AND METHODS

Drosophila culture

Flies were grown on standard medium at 18° C. for optimal imaginal disc growth.

Immunohistochemistry

Antibody staining of eye imaginal discs was performed as described in Gaul et al., 1992, Cell 68:1007–1019. For the Notch/ELAV stainings, mouse mAb C17.9C6 (Fehon et al., 1990, Cell 61:523–534) and rat mAb 7E8A10 (Robinow and White, 1991, J. Neurobiol. 22:443–461) were used at 1:2000 and 1:1 dilutions, respectively. For the Notch/Sevenless double stainings, rat polyclonal Ab Rat5 (R. G. Fehon, I. Rebay, and S. Artavanis-Tsakonas, unpublished) and mouse mAb sev150C3 (Banerjee et al., 1987, Cell 51:151–158) were used at 1:500 and 1:1000 dilutions, respectively. In both cases, goat anti-mouse FITC-conjugated and goat anti-rat Texas Red-conjugated double-label grade secondary antibodies (Jackson ImmunoResearch Laboratories, Inc.) were used at 1:250 and 1:500 dilutions, respectively.

Confocal microscopy

Confocal microscopy and image processing were performed as described by Xu et al., 1992, Development 115:913–922.

6.2. RESULTS

Previous studies on R7 photoreceptor cell determination in Drosophila have shown that specification of neural fate in the R7 precursor cell is initiated by ligand-induced activation of the receptor tyrosine kinase encoded by sevenless (reviewed in Greenwald and Rubin, 1992, Cell 68:271–281), which is expressed strongly in a subset of uncommitted cells in each developing ommatidium, namely the R3, R4, and R7 precursor cells, the four cone cell precursors, and up to two so-called 'mystery cells' (Tomlinson et al., 1987, Cell 51:143–150; Bowtell et al., 1989, Proc. Natl. Acad. Sci. USA 86:6245–6249; Basler et al., 1989, EMBO J. 8:2381–2386). Activation of the Sevenless tyrosine kinase results in the subsequent activation of Ras1 (Simon et al., 1991, Cell 67:701–716; Bonfini et al., 1992, Science 255:603–606), which in turn activates Raf (Dickson et al., 1992, Nature 360:600–603). These studies have also led to the production of transgenic fly lines bearing constitutively activated Sevenless, Ras1, and Raf proteins, all expressed under sevenless gene control in the above mentioned cells (Basler et al., 1991, Cell 64:1069–1081; Fortini et al., 1992, Nature 355:559–561; Dickson et al., 1992, Genes Dev. 6:2327–2339; Dickson et al., Nature 360:600–603). In each case, expression of the activated sevenless pathway component drives sevenless-expressing cells into neural fates, as judged by the expression of neural-specific antigens such as BP-104 (Hortsch et al., 1990, Neuron 4:697–709) or ELAV (Bier et al., 1988, Science 240:913–916; Robinow and White, 1991, J. Neurobiol. 22:443–461) in the eye disc. While the wild-type Notch gene is expressed in and required for normal development of all or most eye disc cells (Cagan and Ready, 1989, Genes Dev. 3:1099–1112; Fehon et al., 1991, J. Cell. Biol. 113:657–669), a constitutively activated Notch receptor lacking the extracellular and transmembrane domains expressed under sevenless gene control blocks cell-fate commitment, preventing ELAV expression in neural precursors and causing cell-fate misspecifications among the sevenless-expressing cells (Fortini et al., 1993, Nature 365:555–557).

To determine whether the block imposed by activated Notch upon neural differentiation can be circumvented by constitutive activation of any of the sevenless signalling pathway components, transgenic flies were produced co-expressing activated Notch and activated sevenless pathway factors in the sevenless-expressing cells. Eye discs of these flies were double-stained with antibodies directed against Notch and against the ELAV protein to determine whether cells expressing activated Notch are capable of neural induction by activated Sevenless, activated Ras, or activated Raf. Since ELAV is a nuclear antigen, we chose to use an activated Notch construct, termed sev-Notch$^{nucl}$, that produces nuclear Notch protein localization (Fortini et al., 1993, Nature 365:555–557). This nuclear Notch expression is easily distinguished from the apical membrane distribution of the endogenous wild-type Notch protein (Fehon et al., 1991, J. Cell. Biol. 113:657–669; Fortini et al., 1993, Nature 365:555–557). Nuclear translocation of the Notch protein apparently is not required for its activated behavior, since the same phenotypic effects are caused by a truncated Notch protein lacking extracellular but not transmembrane sequences that is apically localized, as judged by antibody staining experiments (Fortini et al., 1993, Nature 365:555–557).

The analysis was restricted to the four cone cell precursors of each developing ommatidium for the following reasons. First, the cone cell precursor nuclei are easily identified by their distinctive sausage-shaped morphology. Second, the cone cell precursors are normally non-neural and thus should only be ELAV-positive as a result of the transgene-driven activated sevenless pathway components. Third, Notch expression in sev-Notch$^{nucl}$ cone cell precursor nuclei persists throughout those ommatidial rows of the posterior eye disc in which cone cell precursors exhibit strong ELAV expression if they are transformed into neurons (Fortini et al., 1992, Nature 355:559–561, 1993, Nature 365:555–557; Gaul et al., 1992, Cell 68:1007–1019; Dickson et al., 1992, Nature 360:600–603). By contrast, the nuclear Notch expression in R3 and R4 precursor cells and mystery cells is more transient, subsiding prior to the onset of ELAV expression (Fortini et al., 1993, Nature 365:555–557).

Notch-positive cone cell precursor nuclei were scored for ELAV expression in sev-Notchnucl flies also carrying either the activated Sevenless tyrosine kinase construct sev-S11 (Basler et al., 1991, Cell 64:1069-1081), the activated Ras1 construct sevRas1$^{Val12}$ (Fortini et al., 1992, Nature 355:559-561), or the activated Raf construct sE-raf$^{torY9}$ (Dickson et al., 1992, Genes Dev. 6:2327-2339; Dickson et al., Nature 360:600-603). For each genotype, 500 Notch-positive cone cell precursor nuclei in ommatidial rows 15-25 were examined, representing at least six separate pairs of eye discs. In no case did we observe any cone cell precursor nuclei positive for both Notch and ELAV antigens (FIGS. 5A-5F). We frequently found that not all four cone cell precursor nuclei in an ommatidium express Notch, and that those which do not are often ELAV-positive (FIGS. 5A-5F). These nuclei presumably correspond to cone cell precursors that do not express sev-Notch$^{nucl}$ efficiently but do express sufficient amounts of an activated sevenless pathway molecule to induce neural differentiation. Identical results were obtained with different sev-Notch$^{nucl}$, sev-S11, and sevRas1$^{Val12}$ transgenic lines as well as with an alternative activated Raf construct sE-raf$^{tor4021}$ (Dickson et al., 1992, Genes Dev. 6:2327-2339; Dickson et al., Nature 360:600-603).

To rule out the possibility that our failure to detect co-expression of activated Notch and ELAV antigens in cone cell precursor nuclei is due to some mechanism that prevents two different sevenless promoter constructs from being expressed in the same cell, we double-stained eye discs of transgenic flies bearing both sev-Notchnucl and sev-S11 in a sevenless$^{d2}$ genetic background with antibodies against Notch and against the intracellular 60-kD subunit of Sevenless (Banerjee et al., 1987, Cell 51:151-158). Since sevenless$^{d2}$ flies do not express this subunit (Banerjee et al, 1987), the only Sevenless immunoreactivity detected corresponds to the extracellularly truncated protein produced by the sev-S11 transgene (Basler et al., 1991, Cell 64:1069-1081). It was found that most cone cell precursors showing strong nuclear expression of activated Notch also display strong apical membrane expression of activated Sevenless, demonstrating that both transgenes are coexpressed in these cells (FIGS. 6A-6B).

6.3. DISCUSSION

The class of transmembrane receptor proteins encoded by the Notch locus and related genes appears to regulate a common step in cell-fate selection in organisms ranging from nematodes to humans (reviewed in Greenwald and Rubin, 1992, Cell 68:271-281; Fortini and Artavanis-Tsakonas, 1993, Cell 75:1245-1247). In many different cell types, the signal generated by Notch activation renders cells temporarily unable to respond to developmental cues from neighboring cells (Coffman et al., 1993, Cell 73:659-671; Rebay et al., 1993, Cell 74:319-329; Struhl et al., 1993, Cell 74:331-345; Fortini et al., 1993, Nature 365:555-557; Lieber et al., 1993, Genes Dev. 7:1949-1965). The Notch protein and its ligands Delta and Serrate may thus be part of a general mechanism that limits the competence of undifferentiated cells to undergo cell-fate commitment (Coffman et al., 1993, Cell 73:659-671; Fortini and Artavanis-Tsakonas, 1993, Cell 75:1245-1247). This mechanism may play a crucial role in the timing of inductive events by allowing an uncommitted cell to ignore irrelevant signals from adjacent cells until it is presented with the appropriate inductive signal, presumably preceded or accompanied by a signal that inactivates Notch in the recipient cell. Consistent with this notion, genetic analyses in Caenorhabditis and Drosophila have revealed an interdependence between Notch-mediated signaling and several distinct cell type-specific inductive signaling events (reviewed in Horvitz and Sternberg, 1991, Nature 351:535-541; Artavanis-Tsakonas and Simpson, 1991, Trends Genet. 7:403-408; Greenwald and Rubin, 1992, Cell 68:271-281), although little is known about how the different signals are integrated at the molecular level. We have sought to address this question by performing epistasis tests between a constitutively activated Notch receptor and various activated components of the inductive signalling pathway involving the Sevenless receptor tyrosine kinase, Ras1 and Raf in the developing Drosophila eye.

The results presented here indicate that the Notch receptor protein, in its active state, interferes with the intracellular signal generated by constitutively activated versions of Sevenless, Ras1, and Raf (FIG. 7). Our epistasis data are difficult to reconcile with models in which the Notch protein mediates cell signaling primarily by promoting cell adhesion (Hoppe and Greenspan, 1986, Cell 46:773-783; Greenspan, 1990, New Biologist 2:595-600) or by recruiting cell type-specific receptors and their ligands to specialized membrane regions of polarized epithelia (Singer, 1992, Science 255:1671-1677). Instead, Notch apparently mediates a separate signalling pathway whose input is integrated with that of the Ras1 pathway at some point downstream of Raf, at least in this case. Ras1 and Raf, unlike the sevenless receptor tyrosine kinase, act in many different tissues throughout Drosophila development, as does Notch. For example, genetic studies have identified both Ras1 and Raf as essential components of the signaling pathways initiated by the torso and Drosophila EGF receptor (DER) tyrosine kinases (Ambrosio et al., 1989, Nature 342:288-291; Simon et al., 1991, Cell 67:701-716; Doyle and Bishop, 1993, Genes Dev. 7:633-646; Melnick et al., 1993, Development 118:127-138; Diaz-Benjumea and Hafen, 1994, Development 120:569-578). Moreover, cell-fate specifications involving other types of signalling molecules, such as the Drosophila scabrous, wingless and daughterless gene products, also depend upon Notch gene function (Baker et al., 1990, Science 250:1370-1377; Hing et al., 1994, Mech. Dev., in press; Cummings and Cronmiller, 1994, Development 120:381-394). Thus, the activity state of Notch is likely to play an important regulatory role in modulating signalling by Ras1, Raf, and other signalling molecules in a variety of developmental processes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for expansion of a human precursor cell comprising contacting the cell in vitro with an amount of an agonist of Notch function effective to inhibit differentiation of the cell, and exposing the cell in vitro to cell growth conditions such that the cell proliferates.

2. The method according to claim 1 wherein the precursor cell is of ectodermal origin.

3. The method according to claim 1 wherein the precursor cell is of endodermal origin.

4. The method according to claim 1 wherein the precursor cell is of mesodermal origin.

5. The method according to claim 1 wherein the precursor cell is selected from the group consisting of hematopoietic precursor cells, epithelial precursor cells, kidney precursor cells, neural precursor cells, skin precursor cells, osteoblast precursor cells, chondrocyte precursor cells, and liver precursor cells.

6. The method according to claim 1 wherein the agonist is a Delta protein or a derivative thereof which binds to Notch.

7. The method according to claim 1 wherein the agonist is a Serrate protein or a derivative thereof which binds to Notch.

8. The method according to claim 1 wherein the agonist is an antibody to a Notch protein or a fragment of the antibody containing a binding region thereof.

9. The method according to claim 1 wherein the precursor cell is a hematopoietic stem cell.

10. The method according to claim 1 wherein the precursor cell contains a recombinant nucleic acid encoding a protein of value in the treatment of a human disease or disorder.

11. The method according to claim 1 wherein the agonist is a Delta or Serrate protein and said contacting is carried out by a method comprising exposing the precursor cell to cells recombinantly expressing the agonist.

12. The method according to claim 1 wherein said contacting is carried out by culturing said precursor cell in medium containing a purified agonist in soluble form.

13. The method according to claim 1 wherein substantially no differentiation of the cell occurs.

14. The method according to claim 1 in which said contacting and exposing steps are carried out concurrently.

15. A method for expansion of a precursor cell comprising contacting the cell in vitro with an amount of a soluble agonist of Notch function effective to inhibit differentiation of the cell, and exposing the cell in vitro to cell growth conditions such that the cell proliferates.

16. The method according to claim 15 wherein the precursor cell is selected from the group consisting of hematopoietic precursor cells, epithelial precursor cells, kidney precursor cells, neural precursor cells, skin precursor cells, osteoblast precursor cells, chondrocyte precursor cells, liver precursor cells, and muscle cells.

17. The method according to claim 15 wherein the precursor cell is a hematopoietic stem cell.

18. The method according to claim 15 wherein substantially no differentiation of the cell occurs.

19. The method according to claim 15 wherein the soluble agonist is a derivative of a Delta protein, which derivative binds to a Notch protein.

20. The method according to claim 19 wherein the derivative of Delta consists essentially of the extracellular domain of a Delta protein.

21. The method according to claim 19 wherein the derivative is a fragment of a Delta protein.

22. The method according to claim 15 wherein the soluble agonist is a derivative of a Serrate protein, which derivative binds to a Notch protein.

23. The method according to claim 22 wherein the derivative of Serrate consists essentially of the extracellular domain of a Serrate protein.

24. The method according to claim 22 wherein the derivative is a fragment of a Serrate protein.

25. The method according to claim 15 wherein the soluble agonist is an antibody to a Notch protein or a fragment of the antibody containing a binding region thereof.

26. The method according to claim 15 wherein the precursor cell contains a recombinant nucleic acid encoding a protein of value in the treatment of a disease or disorder.

27. The method according to claim 15 which further comprises after said contacting step the step of introducing into the cell a recombinant nucleic acid encoding a protein of value in the treatment of a disease or disorder.

28. The method according to claim 1 or 15 which further comprises removing the agonist of Notch function and inducing at least some of the resulting expanded cells to differentiate.

29. A method for expansion of a precursor cell comprising recombinantly expressing within the cell an amount of a Deltex protein or fragment thereof which binds to a Notch protein effective to inhibit differentiation of the cells; and exposing the cell in vitro to cell growth conditions such that the cell proliferates.

30. A method for expansion of a hematopoietic precursor cell comprising recombinantly expressing within the cell an amount of a Notch protein consisting essentially of the intracellular domain of a Notch protein effective to inhibit differentiation; and exposing the cell in vitro to cell growth conditions such that the cell proliferates.

31. A method for expansion of an epithelial precursor cell comprising recombinantly expressing within the cell an amount of a Notch protein consisting essentially of the intracellular domain of a Notch protein effective to inhibit differentiation; and exposing the cell in vitro to cell growth conditions such that the cell proliferates.

32. A method for expansion of a liver precursor cell comprising recombinantly expressing within the cell an amount of a Notch protein consisting essentially of the intracellular domain of a Notch protein effective to inhibit differentiation; and exposing the cell in vitro to cell growth conditions such that the cell proliferates.

33. A method for expansion of a human precursor cell comprising contacting the precursor cell in vitro with a second cell wherein the second cell recombinantly expresses on its surface a molecule consisting of at least the extracellular domain of a Notch ligand; and exposing the precursor cell in vitro to cell growth conditions such that the precursor cell proliferates.

34. The method of claim 33 wherein the second cell recombinantly expresses on its surface at least the extracellular domain of a Delta protein.

35. The method of claim 33 wherein the second cell recombinantly expresses on its surface at least the extracellular domain of a Serrate protein.

36. A method for expansion of an hematopoietic precursor cell comprising contacting the precursor cell in vitro with a second cell wherein the second cell recombinantly expresses on its surface a molecule consisting of at least the extracellular domain of a Notch ligand; and exposing the precursor cell in vitro to cell growth conditions such that the precursor cell proliferates.

37. A method for expansion of a human precursor cell comprising contacting the precursor cell in vitro with an amount of a second cell expressing a Notch ligand effective to inhibit differentiation of the cell; and exposing the precursor cell in vitro to cell growth conditions such that the precursor cell proliferates.

38. A method for promoting mammalian neuronal cell growth comprising contacting a mammalian neuron in vitro with an antagonist of Notch function and exposing the neuron in vitro to neuronal cell growth conditions.

39. A method for expansion of a precursor cell comprising contacting the cell in vitro with an amount of a soluble fragment of a Delta protein effective to inhibit differentiation of the cell, and exposing the cell in vitro to cell growth conditions such that the cell proliferates.

40. A method for expansion of a precursor cell comprising contacting the cell in vitro with an amount of a soluble fragment of a Serrate protein effective to inhibit differentiation of the cell, and exposing the cell in vitro to cell growth conditions such that the cell proliferates.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 1015 amino acids
    ( B ) TYPE: amino acid
    ( C ) STRANDEDNESS:
    ( D ) TOPOLOGY: unknown ( i i ) MOLECULE TYPE: protein ( i x ) FEATURE:
    ( A ) NAME/KEY: hum N (Human Notch 2)
    ( B ) LOCATION: 1155...2169
    ( D ) OTHER INFORMATION: Highly conserved ankyrin repeat
        region of Notch ( x i ) SEQUENCE DESCRIPTION: SEQ ID NO:1:

```
Ser  Asn  Pro  Cys  Gln  His  Gly  Ala  Thr  Cys  Ser  Asp  Phe  Ile  Gly  Gly
 1              5                   10                  15

Tyr  Arg  Cys  Glu  Cys  Val  Pro  Gly  Tyr  Gln  Gly  Val  Asn  Cys  Glu  Tyr
               20                  25                  30

Glu  Val  Asp  Glu  Cys  Gln  Asn  Gln  Pro  Cys  Gln  Asn  Gly  Gly  Thr  Cys
          35                  40                      45

Ile  Asp  Leu  Val  Asn  His  Phe  Lys  Cys  Ser  Cys  Pro  Pro  Gly  Thr  Arg
     50                  55                  60

Gly  Leu  Leu  Cys  Glu  Glu  Asn  Ile  Asp  Asp  Cys  Ala  Arg  Gly  Pro  His
 65                 70                  75                          80

Cys  Leu  Asn  Gly  Gly  Gln  Cys  Met  Asp  Arg  Ile  Gly  Gly  Tyr  Ser  Cys
               85                  90                      95

Arg  Cys  Leu  Pro  Gly  Phe  Ala  Gly  Glu  Arg  Cys  Glu  Gly  Asp  Ile  Asn
              100                 105                 110

Glu  Cys  Leu  Ser  Asn  Pro  Cys  Ser  Ser  Glu  Gly  Ser  Leu  Asp  Cys  Ile
              115                 120                 125

Gln  Leu  Thr  Asn  Asp  Tyr  Leu  Cys  Val  Cys  Arg  Ser  Ala  Phe  Thr  Gly
     130                 135                 140

Arg  His  Cys  Glu  Thr  Phe  Val  Asp  Val  Cys  Pro  Gln  Met  Pro  Cys  Leu
145                      150                 155                         160

Asn  Gly  Gly  Thr  Cys  Ala  Val  Ala  Ser  Asn  Met  Pro  Asp  Gly  Phe  Ile
              165                 170                 175

Cys  Arg  Cys  Pro  Pro  Gly  Phe  Ser  Gly  Ala  Arg  Cys  Gln  Ser  Ser  Cys
              180                 185                 190

Gly  Gln  Val  Lys  Cys  Arg  Lys  Gly  Glu  Gln  Cys  Val  His  Thr  Ala  Ser
          195                 200                 205

Gly  Pro  Arg  Cys  Phe  Cys  Pro  Ser  Pro  Arg  Asp  Cys  Glu  Ser  Gly  Cys
     210                 215                 220

Ala  Ser  Ser  Pro  Cys  Gln  His  Gly  Gly  Ser  Cys  His  Pro  Gln  Arg  Gln
225                      230                 235                         240

Pro  Pro  Tyr  Tyr  Ser  Cys  Gln  Cys  Ala  Pro  Pro  Phe  Ser  Gly  Ser  Arg
              245                 250                 255

Cys  Glu  Leu  Tyr  Thr  Ala  Pro  Pro  Ser  Thr  Pro  Pro  Ala  Thr  Cys  Leu
              260                 265                 270

Ser  Gln  Tyr  Cys  Ala  Asp  Lys  Ala  Arg  Asp  Gly  Val  Cys  Asp  Glu  Ala
          275                 280                 285
```

```
Cys Asn Ser His Ala Cys Gln Trp Asp Gly Gly Asp Cys Ser Leu Thr
    290                 295                 300
Met Glu Asn Pro Trp Ala Asn Cys Ser Ser Pro Leu Pro Cys Trp Asp
305                 310                 315                 320
Tyr Ile Asn Asn Gln Cys Asp Glu Leu Cys Asn Thr Val Glu Cys Leu
                325                 330                 335
Phe Asp Asn Phe Glu Cys Gln Gly Asn Ser Lys Thr Cys Lys Tyr Asp
            340                 345                 350
Lys Tyr Cys Ala Asp His Phe Lys Asp Asn His Cys Asn Gln Gly Cys
        355                 360                 365
Asn Ser Glu Glu Cys Gly Trp Asp Gly Leu Asp Cys Ala Ala Asp Gln
370                 375                 380
Pro Glu Asn Leu Ala Glu Gly Thr Leu Val Ile Val Val Leu Met Pro
385                 390                 395                 400
Pro Glu Gln Leu Leu Gln Asp Ala Arg Ser Phe Leu Arg Ala Leu Gly
                405                 410                 415
Thr Leu Leu His Thr Asn Leu Arg Ile Lys Arg Asp Ser Gln Gly Glu
            420                 425                 430
Leu Met Val Tyr Pro Tyr Tyr Gly Glu Lys Ser Ala Ala Met Lys Lys
        435                 440                 445
Gln Arg Met Thr Arg Arg Ser Leu Pro Gly Glu Gln Glu Gln Glu Val
450                 455                 460
Ala Gly Ser Lys Val Phe Leu Glu Ile Asp Asn Arg Gln Cys Val Gln
465                 470                 475                 480
Asp Ser Asp His Cys Phe Lys Asn Thr Asp Ala Ala Ala Ala Leu Leu
                485                 490                 495
Ala Ser His Ala Ile Gln Gly Thr Leu Ser Tyr Pro Leu Val Ser Val
            500                 505                 510
Val Ser Glu Ser Leu Thr Pro Glu Arg Thr Gln Leu Leu Tyr Leu Leu
        515                 520                 525
Ala Val Ala Val Val Ile Ile Leu Phe Ile Ile Leu Leu Gly Val Ile
530                 535                 540
Met Ala Lys Arg Lys Arg Lys His Gly Ser Leu Trp Leu Pro Glu Gly
545                 550                 555                 560
Phe Thr Leu Arg Arg Asp Ala Ser Asn His Lys Arg Arg Glu Pro Val
                565                 570                 575
Gly Gln Asp Ala Val Gly Leu Lys Asn Leu Ser Val Gln Val Ser Glu
            580                 585                 590
Ala Asn Leu Ile Gly Thr Gly Thr Ser Glu His Trp Val Asp Asp Glu
        595                 600                 605
Gly Pro Gln Pro Lys Lys Val Lys Ala Glu Asp Ala Leu Leu Ser
610                 615                 620
Glu Glu Asp Asp Pro Ile Asp Arg Arg Pro Trp Thr Gln Gln His Leu
625                 630                 635                 640
Glu Ala Ala Asp Ile Arg Arg Thr Pro Ser Leu Ala Leu Thr Pro Pro
                645                 650                 655
Gln Ala Glu Gln Glu Val Asp Val Leu Asp Val Asn Val Arg Gly Pro
            660                 665                 670
Asp Gly Cys Thr Pro Leu Met Leu Ala Ser Leu Arg Gly Gly Ser Ser
        675                 680                 685
Asp Leu Ser Asp Glu Asp Glu Asp Ala Glu Asp Ser Ser Ala Asn Ile
690                 695                 700
Ile Thr Asp Leu Val Tyr Gln Gly Ala Ser Leu Gln Ala Gln Thr Asp
705                 710                 715                 720
```

-continued

| | | | | | | | | | | | | | | |
|---|---|---|---|---|---|---|---|---|---|---|---|---|---|---|
| Arg | Thr | Gly | Glu | Met<br>725 | Ala | Leu | His | Leu | Ala<br>730 | Ala | Arg | Tyr | Ser<br>735 | Arg | Ala |
| Asp | Ala | Ala | Lys<br>740 | Arg | Leu | Leu | Asp | Ala<br>745 | Gly | Ala | Asp | Ala | Asn<br>750 | Ala | Gln |
| Asp | Asn | Met<br>755 | Gly | Arg | Cys | Pro | Leu<br>760 | His | Ala | Ala | Val | Ala<br>765 | Ala | Asp | Ala |
| Gln | Gly<br>770 | Val | Phe | Gln | Ile | Leu<br>775 | Ile | Arg | Asn | Arg | Val<br>780 | Thr | Asp | Leu | Asp |
| Ala<br>785 | Arg | Met | Asn | Asp | Gly<br>790 | Thr | Thr | Pro | Leu | Ile<br>795 | Leu | Ala | Ala | Arg | Leu<br>800 |
| Ala | Val | Glu | Gly | Met<br>805 | Val | Ala | Glu | Leu | Ile<br>810 | Asn | Cys | Gln | Ala | Asp<br>815 | Val |
| Asn | Ala | Val | Asp<br>820 | Asp | His | Gly | Lys | Ser<br>825 | Ala | Leu | His | Trp | Ala<br>830 | Ala | Ala |
| Val | Asn | Asn<br>835 | Val | Glu | Ala | Thr | Leu<br>840 | Leu | Leu | Leu | Lys | Asn<br>845 | Gly | Ala | Asn |
| Arg | Asp<br>850 | Met | Gln | Asp | Asn | Lys<br>855 | Glu | Glu | Thr | Pro | Leu<br>860 | Phe | Leu | Ala | Ala |
| Arg<br>865 | Glu | Gly | Ser | Tyr | Glu<br>870 | Ala | Ala | Lys | Ile | Leu<br>875 | Leu | Asp | His | Phe | Ala<br>880 |
| Asn | Arg | Asp | Ile | Thr<br>885 | Asp | His | Met | Asp | Arg<br>890 | Leu | Pro | Arg | Asp | Val<br>895 | Ala |
| Arg | Asp | Arg | Met<br>900 | His | His | Asp | Ile | Val<br>905 | Arg | Leu | Leu | Asp | Glu<br>910 | Tyr | Asn |
| Val | Thr | Pro<br>915 | Ser | Pro | Pro | Gly | Thr<br>920 | Val | Leu | Thr | Ser | Ala<br>925 | Leu | Ser | Pro |
| Val | Ile<br>930 | Cys | Gly | Pro | Asn | Arg<br>935 | Ser | Phe | Leu | Ser | Leu<br>940 | Lys | His | Thr | Pro |
| Met<br>945 | Gly | Lys | Lys | Ser | Arg<br>950 | Arg | Pro | Ser | Ala | Lys<br>955 | Ser | Thr | Met | Pro | Thr<br>960 |
| Ser | Leu | Pro | Asn | Leu<br>965 | Ala | Lys | Glu | Ala | Lys<br>970 | Asp | Ala | Lys | Gly | Ser<br>975 | Arg |
| Arg | Lys | Lys<br>980 | Ser | Leu | Ser | Glu | Lys<br>985 | Val | Gln | Leu | Ser | Glu<br>990 | Ser | Ser | Val |
| Thr | Leu | Ser<br>995 | Pro | Val | Asp | Ser | Leu<br>1000 | Glu | Ser | Pro | His | Thr<br>1005 | Tyr | Val | Ser |
| Asp | Thr<br>1010 | Thr | Ser | Ser | Pro | Met<br>1015 | | | | | | | | | |

( 2 ) INFORMATION FOR SEQ ID NO:2:

( i ) SEQUENCE CHARACTERISTICS:
        ( A ) LENGTH: 1068 amino acids
        ( B ) TYPE: amino acid
        ( C ) STRANDEDNESS:
        ( D ) TOPOLOGY: unknown ( i i ) MOLECULE TYPE: protein ( i x ) FEATURE:
        ( A ) NAME/KEY: Human N1 (TAN-1)
        ( B ) LOCATION: 1152...2219
        ( D ) OTHER INFORMATION: Highly conserved ankyrin repeat
        region of Notch ( x i ) SEQUENCE DESCRIPTION: SEQ ID NO:2:

| | | | | | | | | | | | | | | |
|---|---|---|---|---|---|---|---|---|---|---|---|---|---|---|
| Pro<br>1 | Ser | Pro | Cys | Gln<br>5 | Asn | Gly | Ala | Thr | Cys<br>10 | Thr | Asp | Tyr | Leu | Gly<br>15 | Gly |

```
Tyr Ser Cys Lys Cys Val Ala Gly Tyr His Gly Val Asn Cys Ser Glu
             20                  25                  30
Glu Ile Asp Glu Cys Leu Ser His Pro Cys Gln Asn Gly Gly Thr Cys
         35                  40                  45
Leu Asp Leu Pro Asn Thr Tyr Lys Cys Ser Cys Pro Trp Gly Thr Gln
     50                  55                  60
Gly Val His Cys Glu Ile Asn Val Asp Asp Cys Asn Pro Pro Val Asp
 65                  70                  75                  80
Pro Val Ser Trp Ser Pro Lys Cys Phe Asn Asn Gly Thr Cys Val Asp
             85                  90                  95
Gln Val Gly Gly Tyr Ser Cys Thr Cys Pro Pro Gly Phe Val Gly Glu
             100                 105                 110
Arg Cys Glu Gly Asp Val Asn Glu Cys Leu Ser Asn Pro Cys Asp Ala
         115                 120                 125
Arg Gly Thr Gln Asn Cys Val Gln Arg Val Asn Asp Phe His Cys Glu
     130                 135                 140
Cys Arg Ala Gly His Thr Gly Arg Arg Cys Glu Ser Val Ile Asn Gly
 145                 150                 155                 160
Cys Lys Gly Lys Pro Cys Lys Asn Gly Gly Thr Cys Ala Val Ala Ser
             165                 170                 175
Asn Thr Ala Arg Gly Phe Ile Cys Lys Cys Pro Ala Gly Phe Glu Gly
         180                 185                 190
Ala Thr Cys Glu Asn Asp Ala Arg Thr Cys Gly Ser Leu Arg Cys Leu
     195                 200                 205
Asn Gly Gly Thr Cys Ile Ser Gly Pro Arg Ser Pro Thr Cys Leu Cys
 210                 215                 220
Leu Gly Pro Phe Thr Gly Pro Glu Cys Gln Phe Pro Ala Ser Ser Pro
 225                 230                 235                 240
Cys Leu Gly Gly Asn Pro Cys Tyr Asn Gln Gly Thr Cys Glu Pro Thr
             245                 250                 255
Ser Glu Ser Pro Phe Tyr Arg Cys Leu Cys Pro Ala Lys Phe Asn Gly
         260                 265                 270
Leu Leu Cys His Ile Leu Asp Tyr Ser Phe Gly Gly Gly Ala Gly Arg
     275                 280                 285
Asp Ile Pro Pro Pro Leu Ile Glu Glu Ala Cys Glu Leu Pro Glu Cys
 290                 295                 300
Gln Glu Asp Ala Gly Asn Lys Val Cys Ser Leu Gln Cys Asn Asn His
 305                 310                 315                 320
Ala Cys Gly Trp Asp Gly Gly Asp Cys Ser Leu Asn Phe Asn Asp Pro
             325                 330                 335
Trp Lys Asn Cys Thr Gln Ser Leu Gln Cys Trp Lys Tyr Phe Ser Asp
         340                 345                 350
Gly His Cys Asp Ser Gln Cys Asn Ser Ala Gly Cys Leu Phe Asp Gly
     355                 360                 365
Phe Asp Cys Gln Arg Ala Glu Gly Gln Cys Asn Pro Leu Tyr Asp Gln
 370                 375                 380
Tyr Cys Lys Asp His Phe Ser Asp Gly His Cys Asp Gln Gly Cys Asn
 385                 390                 395                 400
Ser Ala Glu Cys Glu Trp Asp Gly Leu Asp Cys Ala Glu His Val Pro
             405                 410                 415
Glu Arg Leu Ala Ala Gly Thr Leu Val Val Val Val Leu Met Pro Pro
         420                 425                 430
Glu Gln Leu Arg Asn Ser Ser Phe His Phe Leu Trp Glu Leu Ser Arg
     435                 440                 445
```

-continued

| Val | Leu | His | Thr | Asn | Val | Val | Phe | Lys | Arg | Asp | Ala | His | Gly | Gln | Gln |
| | | 450 | | | | 455 | | | | 460 | | | | | |

| Met | Ile | Phe | Pro | Tyr | Tyr | Gly | Arg | Glu | Glu | Glu | Leu | Arg | Lys | His | Pro |
| 465 | | | | | 470 | | | | | 475 | | | | | 480 |

| Ile | Lys | Arg | Ala | Ala | Glu | Gly | Trp | Ala | Ala | Pro | Asp | Ala | Leu | Leu | Gly |
| | | | | 485 | | | | | 490 | | | | | 495 | |

| Gln | Val | Lys | Ala | Ser | Leu | Leu | Pro | Gly | Ser | Glu | Gly | Gly | Trp | Trp |
| | | | 500 | | | | | 505 | | | | 510 | | | |

| Trp | Arg | Glu | Leu | Asp | Pro | Met | Asp | Val | Arg | Gly | Ser | Ile | Val | Tyr | Leu |
| | | 515 | | | | 520 | | | | | 525 | | | | |

| Glu | Ile | Asp | Asn | Trp | Gln | Cys | Val | Gln | Ala | Ser | Ser | Gln | Cys | Phe | Gln |
| | | 530 | | | | 535 | | | | | 540 | | | | |

| Ser | Ala | Thr | Asp | Val | Ala | Ala | Phe | Leu | Gly | Ala | Leu | Ala | Ser | Leu | Gly |
| 545 | | | | | 550 | | | | | 555 | | | | | 560 |

| Ser | Leu | Asn | Ile | Pro | Tyr | Lys | Ile | Glu | Ala | Val | Gln | Ser | Glu | Thr | Val |
| | | | | 565 | | | | | 570 | | | | | 575 | |

| Glu | Pro | Pro | Pro | Pro | Ala | Gln | Leu | His | Phe | Met | Tyr | Val | Ala | Ala | Ala |
| | | | 580 | | | | | 585 | | | | | 590 | | |

| Ala | Phe | Val | Leu | Leu | Phe | Phe | Val | Gly | Cys | Gly | Val | Leu | Leu | Ser | Arg |
| | | 595 | | | | | 600 | | | | | 605 | | | |

| Lys | Arg | Trp | Xaa | Gln | His | Gly | Gln | Leu | Trp | Phe | Pro | Glu | Gly | Phe | Lys |
| | 610 | | | | | 615 | | | | | 620 | | | | |

| Val | Ser | Glu | Ala | Ser | Lys | Lys | Lys | Trp | Trp | Glu | Xaa | Leu | Gly | Glu | Asp |
| 625 | | | | | 630 | | | | | 635 | | | | | 640 |

| Ser | Val | Gly | Leu | Lys | Pro | Leu | Lys | Asn | Ala | Ser | Asp | Gly | Ala | Leu | Met |
| | | | | 645 | | | | | 650 | | | | | 655 | |

| Asp | Asp | Asn | Gln | Asn | Glu | Trp | Gly | Asp | Glu | Asp | Leu | Glu | Thr | Lys | Lys |
| | | | 660 | | | | | 665 | | | | | 670 | | |

| Phe | Trp | Phe | Glu | Glu | Pro | Val | Val | Leu | Pro | Asp | Leu | Asp | Asp | Gln | Thr |
| | | 675 | | | | | 680 | | | | | 685 | | | |

| Asp | His | Trp | Gln | Trp | Thr | Gln | Gln | His | Leu | Asp | Ala | Ala | Asp | Leu | Arg |
| | 690 | | | | | 695 | | | | | 700 | | | | |

| Met | Ser | Ala | Met | Ala | Pro | Thr | Pro | Pro | Gln | Gly | Glu | Val | Asp | Ala | Asp |
| 705 | | | | | 710 | | | | | 715 | | | | | 720 |

| Cys | Met | Asp | Val | Asn | Val | Arg | Gly | Pro | Asp | Gly | Phe | Thr | Pro | Leu | Met |
| | | | | 725 | | | | | 730 | | | | | 735 | |

| Ile | Ala | Ser | Cys | Ser | Gly | Gly | Gly | Leu | Glu | Thr | Gly | Asn | Ser | Glu | Glu |
| | | | 740 | | | | | 745 | | | | | 750 | | |

| Glu | Glu | Asp | Ala | Pro | Ala | Val | Ile | Ser | Asp | Phe | Ile | Tyr | Gln | Gly | Ala |
| | | 755 | | | | | 760 | | | | | 765 | | | |

| Ser | Leu | His | Asn | Gln | Thr | Asp | Arg | Thr | Gly | Glu | Thr | Ala | Leu | His | Leu |
| | 770 | | | | | 775 | | | | | 780 | | | | |

| Ala | Ala | Arg | Tyr | Ser | Arg | Ser | Asp | Ala | Ala | Lys | Arg | Leu | Leu | Glu | Ala |
| 785 | | | | | 790 | | | | | 795 | | | | | 800 |

| Ser | Ala | Asp | Ala | Asn | Ile | Gln | Asp | Asn | Met | Gly | Arg | Thr | Pro | Leu | His |
| | | | | 805 | | | | | 810 | | | | | 815 | |

| Ala | Ala | Val | Ser | Ala | Asp | Ala | Gln | Gly | Val | Phe | Gln | Ile | Leu | Ile | Trp |
| | | | 820 | | | | | 825 | | | | | 830 | | |

| Asn | Arg | Ala | Thr | Asp | Leu | Asp | Ala | Arg | Met | His | Asp | Gly | Thr | Thr | Pro |
| | | 835 | | | | | 840 | | | | | 845 | | | |

| Leu | Ile | Leu | Ala | Ala | Arg | Leu | Ala | Val | Glu | Gly | Met | Leu | Glu | Asp | Leu |
| | 850 | | | | | 855 | | | | | 860 | | | | |

| Ile | Asn | Ser | His | Ala | Asp | Val | Asn | Ala | Val | Asp | Asp | Leu | Gly | Lys | Ser |

-continued

```
865                    870                    875                    880
Ala  Leu  His  Trp  Ala  Ala  Ala  Val  Asn  Asn  Val  Asp  Ala  Ala  Val  Val
                    885                    890                    895
Leu  Leu  Lys  Asn  Gly  Ala  Asn  Lys  Asp  Met  Gln  Asn  Asn  Arg  Glu  Glu
                    900                    905                    910
Thr  Pro  Leu  Phe  Leu  Ala  Ala  Trp  Glu  Gly  Ser  Tyr  Glu  Thr  Ala  Lys
                    915                    920                    925
Val  Leu  Leu  Asp  His  Phe  Ala  Asn  Trp  Asp  Ile  Thr  Asp  His  Met  Asp
          930                    935                    940
Arg  Leu  Pro  Arg  Asp  Ile  Ala  Gln  Glu  Arg  Met  His  His  Asp  Ile  Val
945                    950                    955                    960
Arg  Leu  Leu  Asp  Glu  Tyr  Asn  Leu  Val  Arg  Ser  Pro  Gln  Leu  His  Gly
                    965                    970                    975
Ala  Pro  Leu  Gly  Gly  Thr  Pro  Thr  Leu  Ser  Pro  Pro  Leu  Cys  Ser  Pro
                    980                    985                    990
Asn  Gly  Tyr  Leu  Gly  Ser  Leu  Lys  Pro  Gly  Val  Gln  Gly  Lys  Lys  Val
                    995                    1000                   1005
Arg  Lys  Pro  Ser  Ser  Lys  Gly  Leu  Ala  Cys  Gly  Ser  Lys  Glu  Ala  Lys
          1010                   1015                   1020
Asp  Leu  Lys  Ala  Trp  Arg  Lys  Lys  Ser  Gln  Asp  Gly  Lys  Gly  Cys  Leu
025                    1030                   1035                   1040
Leu  Asp  Ser  Ser  Gly  Met  Leu  Ser  Pro  Val  Asp  Ser  Leu  Glu  Ser  Pro
                    1045                   1050                   1055
His  Gly  Tyr  Leu  Ser  Asp  Val  Ala  Ser  Pro  Pro  Leu
                    1060                   1065
```

( 2 ) INFORMATION FOR SEQ ID NO:3:

( i ) SEQUENCE CHARACTERISTICS:
        ( A ) LENGTH: 1064 amino acids
        ( B ) TYPE: amino acid
        ( C ) STRANDEDNESS:
        ( D ) TOPOLOGY: unknown4

( i i ) MOLECULE TYPE: protein ( i x ) FEATURE:
        ( A ) NAME/KEY: Xen N
        ( B ) LOCATION: 1150...2213
        ( D ) OTHER INFORMATION: Highly conserved ankyrin repeat
            region of Notch ( x i ) SEQUENCE DESCRIPTION: SEQ ID NO:3:

```
Pro  Asn  Pro  Cys  Gln  Asn  Gly  Ala  Thr  Cys  Thr  Asp  Tyr  Leu  Gly  Gly
1                   5                      10                     15
Tyr  Ser  Cys  Glu  Cys  Val  Ala  Gly  Tyr  His  Gly  Val  Asn  Cys  Ser  Glu
                    20                     25                     30
Glu  Ile  Asn  Glu  Cys  Leu  Ser  His  Pro  Cys  Gln  Asn  Gly  Gly  Thr  Cys
          35                     40                     45
Ile  Asp  Leu  Ile  Asn  Thr  Tyr  Lys  Cys  Ser  Cys  Pro  Arg  Gly  Thr  Gln
     50                     55                     60
Gly  Val  His  Cys  Glu  Ile  Asn  Val  Asp  Asp  Cys  Thr  Pro  Phe  Tyr  Asp
65                     70                     75                     80
Ser  Phe  Thr  Leu  Glu  Pro  Lys  Cys  Phe  Asn  Asn  Gly  Lys  Cys  Ile  Asp
                    85                     90                     95
Arg  Val  Gly  Gly  Tyr  Asn  Cys  Ile  Cys  Pro  Pro  Gly  Phe  Val  Gly  Glu
                    100                    105                    110
Arg  Cys  Glu  Gly  Asp  Val  Asn  Glu  Cys  Leu  Ser  Asn  Pro  Cys  Asp  Ser
               115                    120                    125
```

```
Arg Gly Thr Gln Asn Cys Ile Gln Leu Val Asn Asp Tyr Arg Cys Glu
    130             135                 140
Cys Arg Gln Gly Phe Thr Gly Arg Arg Cys Glu Ser Val Val Asp Gly
145             150                 155                 160
Cys Lys Gly Met Pro Cys Arg Asn Gly Gly Thr Cys Ala Val Ala Ser
                165                 170                 175
Asn Thr Glu Arg Gly Phe Ile Cys Lys Cys Pro Pro Gly Phe Asp Gly
            180             185                 190
Ala Thr Cys Glu Tyr Asp Ser Arg Thr Cys Ser Asn Leu Arg Cys Gln
        195             200             205
Asn Gly Gly Thr Cys Ile Ser Val Leu Thr Ser Ser Lys Cys Val Cys
    210             215                 220
Ser Glu Gly Tyr Thr Gly Ala Thr Cys Gln Tyr Pro Val Ile Ser Pro
225             230             235                         240
Cys Ala Ser His Pro Cys Tyr Asn Gly Gly Thr Cys Gln Phe Phe Ala
            245             250                     255
Glu Glu Pro Phe Phe Gln Cys Phe Cys Pro Lys Asn Phe Asn Gly Leu
            260             265                 270
Phe Cys His Ile Leu Asp Tyr Glu Phe Pro Gly Gly Leu Gly Lys Asn
    275             280                 285
Ile Thr Pro Pro Asp Asn Asp Ile Cys Glu Asn Glu Gln Cys Ser
290                 295                 300
Glu Leu Ala Asp Asn Lys Val Cys Asn Ala Asn Cys Asn Asn His Ala
305             310                 315                 320
Cys Gly Trp Asp Gly Gly Asp Cys Ser Leu Asn Phe Asn Asp Pro Trp
            325                 330             335
Lys Asn Cys Thr Gln Ser Leu Gln Cys Trp Lys Tyr Phe Asn Asp Gly
            340             345                 350
Lys Cys Asp Ser Gln Cys Asn Asn Thr Gly Cys Leu Tyr Asp Gly Phe
        355             360             365
Asp Cys Gln Lys Val Glu Val Gln Cys Asn Pro Leu Tyr Asp Gln Tyr
    370             375                 380
Cys Lys Asp His Phe Gln Asp Gly His Cys Asp Gln Gly Cys Asn Asn
385             390             395                     400
Ala Glu Cys Glu Trp Asp Gly Leu Asp Cys Ala Asn Met Pro Glu Asn
            405                 410             415
Leu Ala Glu Gly Thr Leu Val Leu Val Val Leu Met Pro Pro Glu Arg
            420             425                 430
Leu Lys Asn Asn Ser Val Asn Phe Leu Arg Glu Leu Ser Arg Val Leu
        435             440             445
His Thr Asn Val Val Phe Lys Lys Asp Ser Lys Gly Glu Tyr Lys Ile
    450             455                 460
Tyr Pro Tyr Tyr Gly Asn Glu Glu Glu Leu Lys Lys His His Ile Lys
465             470                 475                 480
Arg Ser Thr Asp Tyr Trp Ser Asp Ala Pro Ser Ala Ile Phe Ser Thr
            485             490                 495
Met Lys Glu Ser Ile Leu Leu Gly Arg His Arg Arg Glu Leu Asp Glu
            500                 505                 510
Met Glu Val Arg Gly Ser Ile Val Tyr Leu Glu Ile Asp Asn Arg Gln
        515             520             525
Cys Tyr Lys Ser Ser Ser Gln Cys Phe Asn Ser Ala Thr Asp Val Ala
    530             535                 540
Ala Phe Leu Gly Ala Leu Ala Ser Leu Gly Ser Leu Asp Thr Leu Ser
```

-continued

```
545                         550                         555                         560
Tyr Lys Ile Glu Ala Val Lys Ser Glu Asn Met Glu Thr Pro Lys Pro
                    565                     570                     575
Ser Thr Leu Tyr Pro Met Leu Ser Met Leu Val Ile Pro Leu Leu Ile
                580                     585                     590
Ile Phe Val Phe Met Met Val Ile Val Asn Lys Lys Arg Arg Arg Glu
            595                     600                     605
His Asp Ser Phe Gly Ser Pro Thr Ala Leu Phe Gln Lys Asn Pro Ala
        610                     615                     620
Lys Arg Asn Gly Glu Thr Pro Trp Glu Asp Ser Val Gly Leu Lys Pro
625                     630                     635                     640
Ile Lys Asn Met Thr Asp Gly Ser Phe Met Asp Asp Asn Gln Asn Glu
                    645                     650                     655
Trp Gly Asp Glu Glu Thr Leu Glu Asn Lys Arg Phe Arg Phe Glu Glu
                660                     665                     670
Gln Val Ile Leu Pro Glu Leu Val Asp Asp Lys Thr Asp Pro Arg Gln
            675                     680                     685
Trp Thr Arg Gln His Leu Asp Ala Ala Asp Leu Arg Ile Ser Ser Met
        690                     695                     700
Ala Pro Thr Pro Pro Gln Gly Glu Ile Glu Ala Asp Cys Met Asp Val
705                     710                     715                     720
Asn Val Arg Gly Pro Asp Gly Phe Thr Pro Leu Met Ile Ala Ser Cys
                    725                     730                     735
Ser Gly Gly Gly Leu Glu Thr Gly Asn Ser Glu Glu Glu Glu Asp Ala
                740                     745                     750
Ser Ala Asn Met Ile Ser Asp Phe Ile Gly Gln Gly Ala Gln Leu His
            755                     760                     765
Asn Gln Thr Asp Arg Thr Gly Glu Thr Ala Leu His Leu Ala Ala Arg
        770                     775                     780
Tyr Ala Arg Ala Asp Ala Ala Lys Arg Leu Leu Glu Ser Ser Ala Asp
785                     790                     795                     800
Ala Asn Val Gln Asp Asn Met Gly Arg Thr Pro Leu His Ala Ala Val
                    805                     810                     815
Ala Ala Asp Ala Gln Gly Val Phe Gln Ile Leu Ile Arg Asn Arg Ala
                820                     825                     830
Thr Asp Leu Asp Ala Arg Met Phe Asp Gly Thr Thr Pro Leu Ile Leu
            835                     840                     845
Ala Ala Arg Leu Ala Val Glu Gly Met Val Glu Glu Leu Ile Asn Ala
        850                     855                     860
His Ala Asp Val Asn Ala Val Asp Glu Phe Gly Lys Ser Ala Leu His
865                     870                     875                     880
Trp Ala Ala Ala Val Asn Asn Val Asp Ala Ala Val Leu Leu Lys
                    885                     890                     895
Asn Ser Ala Asn Lys Asp Met Gln Asn Asn Lys Glu Glu Thr Ser Leu
                900                     905                     910
Phe Leu Ala Ala Arg Glu Gly Ser Tyr Glu Thr Ala Lys Val Leu Leu
            915                     920                     925
Asp His Tyr Ala Asn Arg Asp Ile Thr Asp His Met Asp Arg Leu Pro
        930                     935                     940
Arg Asp Ile Ala Gln Glu Arg Met His His Asp Ile Val His Leu Leu
945                     950                     955                     960
Asp Glu Tyr Asn Leu Val Lys Ser Pro Thr Leu His Asn Gly Pro Leu
                    965                     970                     975
```

| Gly | Ala | Thr | Thr 980 | Leu | Ser | Pro | Pro | Ile 985 | Cys | Ser | Pro | Asn | Gly 990 | Tyr | Met |
|---|---|---|---|---|---|---|---|---|---|---|---|---|---|---|---|
| Gly | Asn | Met 995 | Lys | Pro | Ser | Val | Gln 1000 | Ser | Lys | Lys | Ala | Arg 1005 | Lys | Pro | Ser |
| Ile | Lys 1010 | Gly | Asn | Gly | Cys 1015 | Lys | Glu | Ala | Lys | Glu 1020 | Leu | Lys | Ala | Arg | Arg |
| Lys 025 | Lys | Ser | Gln | Asp | Gly 1030 | Lys | Thr | Thr | Leu | Leu 1035 | Asp | Ser | Gly | Ser | Ser 1040 |
| Gly | Val | Leu | Ser | Pro 1045 | Val | Asp | Ser | Leu | Glu 1050 | Ser | Thr | His | Gly | Tyr 1055 | Leu |
| Ser | Asp | Val | Ser 1060 | Ser | Pro | Pro | Leu | | | | | | | | |

( 2 ) INFORMATION FOR SEQ ID NO:4:

( i ) SEQUENCE CHARACTERISTICS:
        ( A ) LENGTH: 1139 amino acids
        ( B ) TYPE: amino acid
        ( C ) STRANDEDNESS:
        ( D ) TOPOLOGY: unknown ( i i ) MOLECULE TYPE: protein ( i x ) FEATURE:
        ( A ) NAME/KEY: Dros N
        ( B ) LOCATION: 1189...2327
        ( D ) OTHER INFORMATION: Highly conserved ankyrin repeat
            region of Notch ( x i ) SEQUENCE DESCRIPTION: SEQ ID NO:4:

| Ser 1 | Gln | Pro | Cys | Gln 5 | Asn | Gly | Gly | Thr | Cys 10 | Arg | Asp | Leu | Ile | Gly 15 | Ala |
|---|---|---|---|---|---|---|---|---|---|---|---|---|---|---|---|
| Tyr | Glu | Cys | Gln 20 | Cys | Arg | Gln | Gly | Phe 25 | Gln | Gly | Gln | Asn | Cys 30 | Glu | Leu |
| Asn | Ile | Asp 35 | Asp | Cys | Ala | Pro | Asn 40 | Pro | Cys | Gln | Asn | Gly 45 | Gly | Thr | Cys |
| His 50 | Asp | Arg | Val | Met | Asn 55 | Phe | Ser | Cys | Ser | Cys 60 | Pro | Pro | Gly | Thr | Met |
| Gly 65 | Ile | Ile | Cys | Glu | Ile 70 | Asn | Lys | Asp | Asp | Cys 75 | Lys | Pro | Gly | Ala | Cys 80 |
| His | Asn | Asn | Gly | Ser 85 | Cys | Ile | Asp | Arg | Val 90 | Gly | Gly | Phe | Glu | Cys 95 | Val |
| Cys | Gln | Pro | Gly 100 | Phe | Val | Gly | Ala | Arg 105 | Cys | Glu | Gly | Asp | Ile 110 | Asn | Glu |
| Cys | Leu | Ser 115 | Asn | Pro | Cys | Ser | Asn 120 | Ala | Gly | Thr | Leu | Asp 125 | Cys | Val | Gln |
| Leu | Val 130 | Asn | Asn | Tyr | His | Cys 135 | Asn | Cys | Arg | Pro | Gly 140 | His | Met | Gly | Arg |
| His 145 | Cys | Glu | His | Lys | Val 150 | Asp | Phe | Cys | Ala | Gln 155 | Ser | Pro | Cys | Gln | Asn 160 |
| Gly | Gly | Asn | Cys | Asn 165 | Ile | Arg | Gln | Ser | Gly 170 | His | His | Cys | Ile | Cys 175 | Asn |
| Asn | Gly | Phe | Tyr 180 | Gly | Lys | Asn | Cys | Glu 185 | Leu | Ser | Gly | Gln | Asp 190 | Cys | Asp |
| Ser | Asn | Pro 195 | Cys | Arg | Val | Gly | Asn 200 | Cys | Val | Val | Ala | Asp 205 | Glu | Gly | Phe |
| Gly | Tyr 210 | Arg | Cys | Glu | Cys | Pro 215 | Arg | Gly | Thr | Leu | Gly 220 | Glu | His | Cys | Glu |
| Ile | Asp | Thr | Leu | Asp | Glu | Cys | Ser | Pro | Asn | Pro | Cys | Ala | Gln | Gly | Ala |

-continued

| 225 | | | | | | 230 | | | | | | 235 | | | | | | 240 |
|---|---|---|---|---|---|---|---|---|---|---|---|---|---|---|---|---|---|---|
| Ala | Cys | Glu | Asp | Leu | Leu | Gly | Asp | Tyr | Glu | Cys | Leu | Cys | Pro | Ser | Lys | | | |
| | | | | 245 | | | | 250 | | | | | | 255 | | | | |
| Trp | Lys | Gly | Lys | Arg | Cys | Asp | Ile | Tyr | Asp | Ala | Asn | Tyr | Pro | Gly | Trp |
| | | | 260 | | | | 265 | | | | | 270 | | | |
| Asn | Gly | Gly | Ser | Gly | Ser | Gly | Asn | Asp | Arg | Tyr | Ala | Ala | Asp | Leu | Glu |
| | | 275 | | | | 280 | | | | | 285 | | | | |
| Gln | Gln | Arg | Ala | Met | Cys | Asp | Lys | Arg | Gly | Cys | Thr | Glu | Lys | Gln | Gly |
| | 290 | | | | 295 | | | | | 300 | | | | | |
| Asn | Gly | Ile | Cys | Asp | Ser | Asp | Cys | Asn | Thr | Tyr | Ala | Cys | Asn | Phe | Asp |
| 305 | | | | 310 | | | | 315 | | | | | | | 320 |
| Gly | Asn | Asp | Cys | Ser | Leu | Gly | Ile | Asn | Pro | Trp | Ala | Asn | Cys | Thr | Ala |
| | | | | 325 | | | | 330 | | | | | | 335 | |
| Asn | Glu | Cys | Trp | Asn | Lys | Phe | Lys | Asn | Gly | Lys | Cys | Asn | Glu | Glu | Cys |
| | | | 340 | | | | 345 | | | | | 350 | | | |
| Asn | Asn | Ala | Ala | Cys | His | Tyr | Asp | Gly | His | Asp | Cys | Glu | Arg | Lys | Leu |
| | | 355 | | | | 360 | | | | 365 | | | | | |
| Lys | Ser | Cys | Asp | Thr | Leu | Phe | Asp | Ala | Tyr | Cys | Gln | Lys | His | Tyr | Gly |
| | 370 | | | | 375 | | | | | 380 | | | | | |
| Asp | Gly | Phe | Cys | Asp | Tyr | Gly | Cys | Asn | Asn | Ala | Glu | Cys | Ser | Trp | Asp |
| 385 | | | | 390 | | | | | 395 | | | | | | 400 |
| Gly | Leu | Asp | Cys | Glu | Asn | Lys | Thr | Gln | Ser | Pro | Val | Leu | Ala | Glu | Gly |
| | | | | 405 | | | | 410 | | | | | 415 | | |
| Ala | Met | Ser | Val | Val | Met | Leu | Met | Asn | Val | Glu | Ala | Phe | Arg | Glu | Ile |
| | | | 420 | | | | 425 | | | | | 430 | | | |
| Gln | Ala | Gln | Phe | Leu | Arg | Asn | Met | Ser | His | Met | Leu | Arg | Thr | Thr | Val |
| | | 435 | | | | 440 | | | | | 445 | | | | |
| Arg | Leu | Lys | Lys | Asp | Ala | Leu | Gly | His | Asp | Ile | Ile | Ile | Asn | Trp | Lys |
| | 450 | | | | 455 | | | | 460 | | | | | | |
| Asp | Asn | Val | Arg | Val | Pro | Glu | Ile | Glu | Asp | Thr | Asp | Phe | Ala | Arg | Lys |
| 465 | | | | 470 | | | | 475 | | | | | | | 480 |
| Asn | Lys | Ile | Leu | Tyr | Thr | Gln | Gln | Val | His | Gln | Thr | Gly | Ile | Gln | Ile |
| | | | 485 | | | | 490 | | | | | 495 | | | |
| Tyr | Leu | Glu | Ile | Asp | Asn | Arg | Lys | Cys | Thr | Glu | Cys | Phe | Thr | His | Ala |
| | | 500 | | | | 505 | | | | 510 | | | | | |
| Val | Glu | Ala | Ala | Glu | Phe | Leu | Ala | Ala | Thr | Ala | Ala | Lys | His | Gln | Leu |
| | | 515 | | | | 520 | | | | 525 | | | | | |
| Arg | Asn | Asp | Phe | Gln | Ile | His | Ser | Val | Arg | Gly | Ile | Lys | Asn | Pro | Gly |
| | 530 | | | | 535 | | | | 540 | | | | | | |
| Asp | Glu | Asp | Asn | Gly | Glu | Pro | Pro | Ala | Asn | Val | Lys | Tyr | Val | Ile | Thr |
| 545 | | | | 550 | | | | 555 | | | | | | | 560 |
| Gly | Ile | Ile | Leu | Val | Ile | Ile | Ala | Leu | Ala | Phe | Phe | Gly | Met | Val | Leu |
| | | | 565 | | | | 570 | | | | | 575 | | | |
| Ser | Thr | Gln | Arg | Lys | Arg | Ala | His | Gly | Val | Thr | Trp | Phe | Pro | Glu | Gly |
| | | 580 | | | | 585 | | | | 590 | | | | | |
| Phe | Arg | Ala | Pro | Ala | Ala | Val | Met | Ser | Arg | Arg | Arg | Arg | Asp | Pro | His |
| | | 595 | | | | 600 | | | | 605 | | | | | |
| Gly | Gln | Glu | Met | Arg | Asn | Leu | Asn | Lys | Gln | Val | Ala | Met | Gln | Ser | Gln |
| | 610 | | | | 615 | | | | 620 | | | | | | |
| Gly | Val | Gly | Gln | Pro | Gly | Ala | His | Trp | Ser | Asp | Glu | Ser | Asp | Met |
| 625 | | | | | 630 | | | | 635 | | | | | 640 |
| Pro | Leu | Pro | Lys | Arg | Gln | Arg | Ser | Asp | Pro | Val | Ser | Gly | Val | Gly | Leu |
| | | | | 645 | | | | 650 | | | | | 655 | | |

-continued

| | | | | | | | | | | | | | |
|---|---|---|---|---|---|---|---|---|---|---|---|---|---|
| Gly | Asn | Asn | Gly 660 | Gly | Tyr | Ala | Ser | Asp 665 | His | Thr | Met | Val | Ser 670 | Glu | Tyr |
| Glu | Glu | Ala 675 | Asp | Gln | Arg | Val | Trp 680 | Ser | Gln | Ala | His | Leu 685 | Asp | Val | Val |
| Asp | Val 690 | Arg | Ala | Ile | Met | Thr 695 | Pro | Pro | Ala | His | Gln 700 | Asp | Gly | Gly | Lys |
| His 705 | Asp | Val | Asp | Ala | Arg 710 | Gly | Pro | Cys | Gly | Leu 715 | Thr | Pro | Leu | Met | Ile 720 |
| Ala | Ala | Val | Arg | Gly 725 | Gly | Gly | Leu | Asp | Thr 730 | Gly | Glu | Asp | Ile | Glu 735 | Asn |
| Asn | Glu | Asp | Ser 740 | Thr | Ala | Gln | Val | Ile 745 | Ser | Asp | Leu | Leu | Ala 750 | Gln | Gly |
| Ala | Glu | Leu 755 | Asn | Ala | Thr | Met | Asp 760 | Lys | Thr | Gly | Glu | Thr 765 | Ser | Leu | His |
| Leu | Ala 770 | Ala | Arg | Phe | Ala | Arg 775 | Ala | Asp | Ala | Ala | Lys 780 | Arg | Leu | Phe | His |
| Ala 785 | Gly | Ala | Asp | Ala | Asn 790 | Cys | Gln | Asp | Asn | Thr 795 | Gly | Arg | Thr | Pro | Leu 800 |
| His | Ala | Ala | Val | Ala 805 | Ala | Asp | Ala | Met | Gly 810 | Val | Phe | Gln | Ile | Leu 815 | Leu |
| Arg | Asn | Arg | Ala 820 | Thr | Asn | Leu | Asn | Ala 825 | Arg | Met | His | Asp | Gly 830 | Thr | Thr |
| Pro | Leu | Ile 835 | Leu | Ala | Ala | Arg | Leu 840 | Ala | Ile | Glu | Gly | Met 845 | Val | Glu | Asp |
| Leu | Ile 850 | Thr | Ala | Asp | Ala | Asp 855 | Ile | Asn | Ala | Ala | Asp 860 | Asn | Ser | Gly | Lys |
| Thr 865 | Ala | Leu | His | Trp | Ala 870 | Ala | Ala | Val | Asn | Thr 875 | Glu | Ala | Val | Asn 880 |
| Ile | Leu | Leu | Met | His 885 | His | Ala | Asn | Arg | Asp 890 | Ala | Gln | Asp | Asp | Lys 895 | Asp |
| Glu | Thr | Pro | Leu 900 | Phe | Leu | Ala | Ala | Arg 905 | Glu | Gly | Ser | Tyr | Glu 910 | Ala | Cys |
| Lys | Ala | Leu 915 | Leu | Asp | Asn | Phe | Ala 920 | Asn | Arg | Glu | Ile | Thr 925 | Asp | His | Met |
| Asp | Arg 930 | Leu | Pro | Arg | Asp | Val 935 | Ala | Ser | Glu | Arg | Leu 940 | His | His | Asp | Ile |
| Val 945 | Arg | Leu | Leu | Asp | Glu 950 | His | Val | Pro | Arg | Ser 955 | Pro | Gln | Met | Leu | Ser 960 |
| Met | Thr | Pro | Gln | Ala 965 | Met | Ile | Gly | Ser | Pro 970 | Pro | Gly | Gln | Gln 975 | Gln |
| Pro | Gln | Leu | Ile 980 | Thr | Gln | Pro | Thr | Val 985 | Ile | Ser | Ala | Gly | Asn 990 | Gly | Gly |
| Asn | Asn | Gly 995 | Asn | Gly | Asn | Ala | Ser 1000 | Gly | Lys | Gln | Ser | Asn 1005 | Gln | Thr | Ala |
| Lys | Gln 1010 | Lys | Ala | Ala | Lys | Lys 1015 | Ala | Lys | Leu | Ile | Glu 1020 | Gly | Ser | Pro | Asp |
| Asn 1025 | Gly | Leu | Asp | Ala | Thr 1030 | Gly | Ser | Leu | Arg | Arg 1035 | Lys | Ala | Ser | Ser | Lys 1040 |
| Lys | Thr | Ser | Ala | Ala 1045 | Ser | Lys | Lys | Ala | Ala 1050 | Asn | Leu | Asn | Gly | Leu 1055 | Asn |
| Pro | Gly | Gln | Leu 1060 | Thr | Gly | Gly | Val | Ser 1065 | Gly | Val | Pro | Gly | Val 1070 | Pro | Pro |
| Thr | Asn | Ser 1075 | Ala | Val | Gln | Ala | Ala 1080 | Ala | Ala | Ala | Ala 1085 | Ala | Val | Ala |

```
Ala Met Ser His Glu Leu Glu Gly Ser Pro Val Gly Val Gly Met Gly
    1090            1095             1100

Gly Asn Leu Pro Ser Pro Tyr Asp Thr Ser Ser Met Tyr Ser Asn Ala
105             1110             1115                    1120

Met Ala Ala Pro Leu Ala Asn Gly Asn Pro Asn Thr Gly Ala Lys Gln
                1125             1130              1135

Pro Pro Ser
```